(12) United States Patent
Lasek et al.

(10) Patent No.: US 7,105,315 B2
(45) Date of Patent: Sep. 12, 2006

(54) TRANSMEMBRANE PROTEIN DIFFERENTIALLY EXPRESSED IN CANCER

(75) Inventors: Amy K. W. Lasek, Oakland, CA (US); Mariah R. Baughn, San Leandro, CA (US); Yalda Azimzai, Oakland, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 686 days.

(21) Appl. No.: 10/187,657

(22) Filed: Jul. 1, 2002

(65) Prior Publication Data
US 2003/0068311 A1 Apr. 10, 2003

Related U.S. Application Data

(63) Continuation-in-part of application No. PCT/US00/07817, filed on Mar. 22, 2000.

(60) Provisional application No. 60/139,565, filed on Jun. 16, 1999.

(51) Int. Cl.
C12N 15/12 (2006.01)
C12N 15/63 (2006.01)
C12N 5/10 (2006.01)
C12P 21/02 (2006.01)

(52) U.S. Cl. .............. 435/69.1; 435/252.3; 435/320.1; 435/325; 530/350; 536/23.1; 536/23.5

(58) Field of Classification Search .................... None
See application file for complete search history.

(56) References Cited

OTHER PUBLICATIONS

GenBank Accession No. AI304327, Feb. 1, 1999.*

Haynes et al. (1998). Proteome analysis: biological assay or data archive. Electrophoresis 19: 1862-1871.*

Hu et al. (2003). Analysis of genomic and proteomic data using advanced literature mining. Journal of Proteome Research. 2:405-412.*

Chen et al. (2002). Discordant protein and mRNA expression in lung adenocarcinomas. Molecular and Cellular Proteomics. 1:304-313.*

GenBank Accession No. AI281211, Jan. 28, 1999.*

Cohen et al. "Cancer: Principles and Practices of Oncology", In: DeVita, Lippincott, Williams & Wilkins, pp. 1148-1149 (2001).

El-Deiry et al. "High expression of the DNA methyltransferase gene characterizes human neoplastic cells and progression stages of colon cancer", *Proc. Natl. Acad. Sci.*, vol. 88, pp. 3470-3474, Apr. 1991.

Issa et al. "Methylation of the oestrogen receptor CpG island links ageing and neoplasia in human colon" *Nature Genetics*, vol. 7, pp. 536-540, Aug. 1994.

Bradley et al. "Increased expression of the epidermal growth factor receptor on human colon carcinoma cells"*Arch Sug*, Nov. 1986 ABSTRACT.

Jass et al. "Hyperplastic polyps and DNA microsatellite unstable cancers of the colorectum", *Histopathology*, vol. 37, pp. 395-301, 2000.

* cited by examiner

Primary Examiner—Lorraine Spector
Assistant Examiner—Jon M. Lockard
(74) Attorney, Agent, or Firm—Foley & Lardner LLP

(57) ABSTRACT

The invention provides a transmembrane protein that is differentially expressed in neoplastic disorders. It also provides for the use of the protein, a cDNA encoding the protein, and antibodies that specifically bind the protein in various methods to diagnose, stage, treat, or monitor the treatment of a neoplastic disorder.

9 Claims, 14 Drawing Sheets

```
                                     11              20             29             38              47             56
5' ACC AGG AAA GTA ACG GCT ACA GAC AGT GAG AAA TAG TTT CGC TCG CCG GCT AGA 65              74             83             92             101            110
AAA ACT CTG TCG GTA CCA ACC CCA GAG CGT TGA GAG CAG CCC ACC TCC ACG CTT 119             128            137            146            155            164
CCT TAA CGG AGA GGT GCA GGA CTC AGA CTT CAC CAG CCC ACT CGG TCC CAG CCT 173             182            191            200            209            218
TGT ACG CAA AGA GAC GCC AAG GAC GCG CTC TCC CGC GTC CAG GCA GCC CCA GCT 227             236            245            254            263            272
TGC CTT GCC TGC CCG CCT GCG TGC AGC ACT CGG TGC AGC GCC CCG GCG ATG ACC
                                                                            M   T 281             290            299            308            317            326
CTG TGG AAC GGC GTA CTG CCT TTT TAC CCC CAG CCC CGG CAT GCC GCA GGC TTC
 L   W   N   G   V   L   P   F   Y   P   Q   P   R   H   A   A   G   F 335             344            353            362            371            380
AGC GTT CCA CTG CTC ATC GTT ATT CTA GTG TTT TTG GCT CTA GTG GCA AGC TTC
 S   V   P   L   L   I   V   I   L   V   F   L   A   L   V   A   S   F
```

FIGURE 1A

```
     389                398                407                416                425                434
CTG  CTC  ATC           TTG  CCG  GGG      ATC  CGT  GGC      CAC  TCG  CGC      TGG  TTT  TGG      TTG  GTG  AGA
 L    L    I             L    P    G       I    R    G        H    S    R        W    F    W        L    V    R 443                452                461                470                479                488
GTT  CTT  CTC           AGT  CTG  TTC      ATA  GGC  GCA      GAA  ATT  GTG      GCT  GTG  CAC      TTC  AGT  GCA
 V    L    L             S    L    F       I    G    A        E    I    V        A    V    H        F    S    A 497                506                515                524                533                542
GAA  TGG  TTC           GTG  GGT  ACA      GTG  AAC  ACC      AAC  ACA  TCC      TAC  AAA  CAC      TTC  AGC  GCA
 E    W    F             V    G    T       V    N    T        N    T    S        Y    K    H        F    S    A 551                560                569                578                587                596
GCG  CGT  GTT           ACA  GCC  CGT      GTC  GGT  CTG      CTG  AAC  CAG      CTG  GGC  CTG      GAG  ATT  ATT
 A    R    V             T    A    R       V    G    L        L    N    Q        L    G    L        E    I    I 605                614                623                632                641                650
ACA  CTC  ACA           GGG  ACC  CCA      GTG  CAT  CAG      CTG  AAC  GAG      ACC  ATT  GAC      TAC  AAC  GAG
 T    L    T             G    T    P       V    H    Q        L    N    E        T    I    D        Y    N    E 659                668                677                686                695                704
CAG  TTC  ACC           TGG  CGT  CTG      AAA  GAG  CAT      AAT  TAC  GCC      GAG  TAC  AAC      GCA  CTG
 Q    F    T             W    R    L       K    E    H        N    Y    A        E    Y    N        A    L 713                722                731                740                749                758
GAG  AAG  GGG           CTG  CCG  GAC      CCA  GTG  CTG      TAC  CTC  TAC      GCG  GAG  AAG      TTC  ACA  CCG  AGT
 E    K    G             L    P    D       P    V    L        Y    L    Y        A    E    K        F    T    P    S
```

FIGURE 1B

```
      767         776         785         794         803         812
AGC CCT TGC GGC CTG TAC CAC CAG TAC CAC CTG GCG GGA CAC TAC GCC TCG GCC
 S   P   C   G   L   Y   H   Q   Y   H   L   A   G   H   Y   A   S   A
      821         830         839         848         857         866
ACG CTA TGG GTG GCG TTC TGC TTC TGG CTC CTC TCC AAC GTG CTG CTC TCC ACG
 T   L   W   V   A   F   C   F   W   L   L   S   N   V   L   L   S   T
      875         884         893         902         911         920
CCG GCC CCG CTC TAC GGA GGC CTG GCA CTG CTG ACC ACC GGA GCC TTC GCG CTC
 P   A   P   L   Y   G   G   L   A   L   L   T   T   G   A   F   A   L
      929         938         947         956         965         974
TTC GGG GTC TTC GCC TTG GCC TCC ATC TCT AGC GTG CCG CTC TGC CCG CTC CGC
 F   G   V   F   A   L   A   S   I   S   S   V   P   L   C   P   L   R
      983         992         1001        1010        1019        1028
CTA GGC TCC TGC CTC ACC ACT CAG TAC GGC GCC TTC TGG GTC ACG CTG
 L   G   S   A   L   T   T   Q   Y   G   A   F   W   V   T   L
      1037        1046        1055        1064        1073        1082
GCA ACC GGC GTC CTG TGC CTC TTC CTC GGA GGG GCC GTG GTG AGT CTC CAG TAT
 A   T   G   V   L   C   L   F   L   G   G   A   V   V   S   L   Q   Y
      1091        1100        1109        1118        1127        1136
GTT CGG CCC AGC GCT CTT CGC ACC CTT CTG GAC CAA AGC GCC AAG GAC TGC AGC
 V   R   P   S   A   L   R   T   L   L   D   Q   S   A   K   D   C   S

FIGURE 1C
```

```
      1145                  1154           1163              1172              1181              1190
CAG GAG AGA GGG GGC TCA CCT CTT ATC CTC GGC GAC CCA CTG CAC AAG CAG GCC
 Q   E   R   G   G   S   P   L   I   L   G   D   P   L   H   K   Q   A
      1199                  1208              1217              1226              1235              1244
GCT CTC CCA GAC TTA AAA TGT ATC ACC ACT AAC CTG TGA GGG GGA CCC AAT CTG
 A   L   P   D   L   K   C   I   T   T   N   L   *   G   G   P   N   L
      1253              1262              1271              1280              1289              1298
GAC TCC TTC CCC GCC TTG GGA CAT CGC AGG CCG AGC AGT GCC CGC CAG GCC
 D   S   F   P   A   L   G   H   R   R   P   S   S   A   R   Q   A
      1307              1316              1325              1334              1343              1352
TGG GCC AGG AGA GCT CCA GGA AGG GCA CTG AGC GCT GCT GGC AGG CCT CGG
 W   A   R   R   A   P   G   R   A   L   S   A   A   G   R   P   R
      1361              1370              1379              1388              1397              1406
ACA TCC GCA GGC ACC AGG GAA AGT CTC CTG GGG CGA TCT GTA AAT AAA CCT TTT
 T   S   A   G   T   R   E   S   L   L   G   R   S   V   N   K   P   F
      1415
TTT CTT TTG TTT TTT  3'
 F   L   L   F   F
```

FIGURE 1D

TRANSMEMBRANE PROTEIN DIFFERENTIALLY EXPRESSED IN CANCER

This is a continuation-in-part application of PCT Application No. PCT/US00/07817, filed Mar. 22, 2000, which claims the benefit of Provisional Application Ser. No. 60/139,565, filed 16 Jun. 1999.

FIELD OF THE INVENTION

This invention relates to a transmembrane protein, its encoding cDNA, and an antibody that specifically binds the protein and to their use to diagnose, to stage, to treat, or to monitor the progression or treatment of neoplastic disorders and in particular colon and lung cancers.

BACKGROUND OF THE INVENTION

Cancers and malignant tumors are characterized by continuous cell proliferation and cell death and are related causally to both genetics and the environment. In developed countries, colorectal cancer is the second most commonly diagnosed cancer, and 95% of the cancers are adenocarcinomas. These cancers are slow growing, and a long interval may elapse before symptoms emerge. Early detection of colorectal cancer significantly impacts survival. A fact of note is that colon cancer is more common in women, and rectal cancer is more common in men. Colorectal cancers spread by direct extension through the bowel wall and metastasis.

Although genetic predisposition is low, colon cancer families include familial adenomatous polyposis, caused by inherited mutations in the APC gene, and hereditary non-polyposis colorectal cancer, caused by mutations in DNA mismatch repair genes leading to increased replication errors in microsatellites. These syndromes are known to occur across several generations and usually present before age 40. Unknown genetic susceptibility factors are thought to occur in "sporadic" colon cancers, because risk increases with persons having first-degree relatives that develop colon cancer before the age of 60 (Cohen et al. In: DeVita (2001) *Cancer: Principles and Practice of Oncology*. Lippincott Williams & Wilkins, Philadelphia Pa., pp. 1148–1149.

Cancer markers are of importance in determining familial predisposition to cancers. For example, even though elevated serum carcinoembryonic antigen (CEA) is not specifically associated with colorectal cancer, its levels are high in 70% of patients. If CEA is high preoperatively and low after removal of a colon tumor, monitoring CEA may help to detect recurrence. In addition, key genes in several molecular pathways may be activated, or genes suppressing cell proliferation may be lost by mutation or by hypermethylation (Wafik et al. (1991) Proc Natl Acad Sci 88:3470–3474; Issa et al. (1994) Nature Genet 7:536–540). Among these are well known tumor suppressors, APC and p53, transmembrane receptors such as the EGF receptor and the guanylyl cyclase C receptor (Bradley et al. (1986) Arch Surg 121:1242–7), G-protein activators such as Ras, and markers associated with CpG islands (Jass et al. (2000) Histopathology 37:295–301). Tumor markers more specifically associated with particular colorectal cancers would be of even greater diagnostic and prognostic utility.

Array technologies and quantitative PCR provide the means to explore the expression profiles of a large number of related or unrelated genes. When an expression profile is examined, arrays provide a platform for examining which genes are tissue-specific, carrying out housekeeping functions, parts of a signaling cascade, or specifically related to a particular genetic predisposition, condition, disease, or disorder. The application of expression profiling is particularly relevant to improving diagnosis, prognosis, and treatment of the disease. For example, both the sequences and the amount of expression can be compared between tissues from subjects with different types of colon cancer and cytologically normal colon tissue.

The discovery of a transmembrane protein, its encoding cDNA, and the making of an antibody that specifically binds the protein satisfies a need in the art by providing compositions which are useful to diagnose, to stage, to treat, or to monitor the progression or treatment of neoplastic disorders and in particular colon and lung cancers.

SUMMARY OF THE INVENTION

The invention is based on the discovery of a transmembrane protein that has been designated CTTP, its encoding cDNA, and an antibody that specifically binds the protein which are useful to diagnose, to stage, to treat, or to monitor the progression or treatment of a neoplastic disorder and in particular colon and lung cancers.

The invention provides an isolated cDNA comprising a nucleic acid sequence encoding a protein having the amino acid sequence of SEQ ID NO:1. The invention also provides an isolated cDNA or the complement thereof selected from a nucleic acid sequence of SEQ ID NO: 2; a fragment selected from SEQ ID NOs:3–7 or from about nucleotide GI to about nucleotide T332, from about nucleotide C479 to about nucleotide C847, from about nucleotide G500 to about nucleotide G792, and from about nucleotide G1083 to about nucleotide G1226 of SEQ ID NO: 2; an oligonucleotide extending from about nucleotide C512 to about nucleotide G575 of SEQ ID NO: 2; and a homolog of SEQ ID NO:2 selected from SEQ ID NOs:8 and 9. The invention further provides a probe consisting of the cDNA encoding the transmembrane protein, A cell transformed with the cDNA encoding the transmembrane protein, a composition comprising the cDNA encoding the transmembrane protein, and a labeling moiety, an array element comprising the cDNA encoding the transmembrane protein, and a substrate upon which the cDNA encoding the transmembrane protein, is immobilized.

The invention provides a vector containing the cDNA encoding CTTP, a host cell containing the vector and a method for using the cDNA to make the protein, the method comprising culturing the host cell containing the vector containing the cDNA encoding the protein under conditions for expression and recovering the protein from the host cell culture. The invention also provides a transgenic cell line or organism comprising the vector containing the cDNA encoding CTTP. The invention further provides a composition, a substrate or a probe comprising the cDNA, a fragment, a variant, or complements thereof, which can be used in methods of detection, screening, and purification. In one aspect, the probe is a single-stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose a neoplastic disorder such as colon or lung cancer.

The invention provides a method for using a cDNA to screen a library or plurality of molecules or compounds to identify at least one ligand which specifically binds the cDNA, the method comprising combining the cDNA with the molecules or compounds under conditions to allow specific binding and detecting specific binding to the cDNA, thereby identifying a ligand which specifically binds the cDNA. In one aspect, the molecules or compounds are selected from antisense molecules, artificial chromosome constructions, branched nucleic acids, DNA molecules, enhancers, peptides, peptide nucleic acids, proteins, RNA molecules, repressors, and transcription factors. The invention also provides a method for using a cDNA to purify a ligand which specifically binds the cDNA, the method comprising attaching the cDNA to a substrate, contacting the cDNA with a sample under conditions to allow specific binding, and dissociating the ligand from the cDNA, thereby obtaining purified ligand. The invention further provides a method for assessing efficacy or toxicity of a molecule or compound comprising treating a sample containing nucleic acids with the molecule or compound; hybridizing the nucleic acids with the cDNA of claim 2 under conditions for hybridization complex formation, determining the amount of complex formation; and comparing the amount of complex formation in the treated sample with the amount of complex formation in an untreated sample, wherein a difference in complex formation indicates the efficacy or toxicity of the molecule or compound.

The invention provides a purified protein or a portion thereof selected from the group consisting of an amino acid sequence of SEQ ID NO:1, a variant having at least 85% identity to the amino acid sequence of SEQ ID NO:1, an oligopeptide extending from about residue D110 to about residue A124 of SEQ ID NO: 1, and a biologically active peptide selected from about residue M1 to about residue V22 or from about residue V273 to about residue 1320 of SEQ ID NO: 1. The invention also provides a composition comprising the purified protein and a pharmaceutical carrier, a composition comprising the protein and a labeling moiety, a substrate upon which the protein is immobilized, and an array element comprising the protein. The invention further provides a method for detecting expression of a protein having the amino acid sequence of SEQ ID NO:1 in a sample, the method comprising performing an assay to determine the amount of the protein in a sample; and comparing the amount of protein to standards, thereby detecting expression of the protein in the sample. The invention still further provides a method for diagnosing cancer comprising performing an assay to quantify the amount of the protein expressed in a sample and comparing the amount of protein expressed to standards, thereby diagnosing a neoplastic disorder. In a one aspect, the assay is selected from antibody arrays, enzyme-linked immunosorbent assays, fluorescence-activated cell sorting, 2D-PAGE and scintillation counting, protein arrays, radioimmunoassays, and western analysis. In a second aspect, the sample is selected from colon, liver, lung, ovary, and prostate. In a third aspect, the disorder is colon or lung cancer.

The invention provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from agonists, antagonists, bispecific molecules, DNA molecules, small drug molecules, immunoglobulins, inhibitors, mimetics, multispecific molecules, peptides, peptide nucleic acids, pharmaceutical agent, proteins, and RNA molecules. In another aspect, the ligand is used to treat a subject with a neoplastic disorder. The invention also provides an therapeutic antibody that specifically binds the protein having the amino acid sequence of SEQ ID NO:1. The invention further provides an antagonist which specifically binds the protein having the amino acid sequence of SEQ ID NO:1. The invention yet further provides a small drug molecule which specifically binds the protein having the amino acid sequence of SEQ ID NO:1. The invention also provides a method for testing ligand for effectiveness as an agonist or antagonist comprising exposing a sample comprising the protein to the molecule or compound, and detecting agonist or antagonist activity in the sample.

The invention provides a method for using a protein to screen a plurality of antibodies to identify an antibody that specifically binds the protein comprising contacting a plurality of antibodies with the protein under conditions to form an antibody:protein complex, and dissociating the antibody from the antibody:protein complex, thereby obtaining antibody that specifically binds the protein. In one aspect the antibodies are selected from intact immunoglobulin molecule, a polyclonal antibody, a monoclonal antibody, a bispecific molecule, a multispecific molecule, a chimeric antibody, a recombinant antibody, a humanized antibody, single chain antibodies, a Fab fragment, an F(ab')$_2$ fragment, an Fv fragment, and an antibody-peptide fusion protein. The invention provides purified antibodies which bind specifically to a protein.

The invention also provides methods for using a protein to prepare and purify polyclonal and monoclonal antibodies which specifically bind the protein. The method for preparing a polyclonal antibody comprises immunizing a animal with protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified polyclonal antibodies. The method for preparing a monoclonal antibodies comprises immunizing a animal with a protein under conditions to elicit an antibody response, isolating antibody producing cells from the animal, fusing the antibody producing cells with immortalized cells in culture to form monoclonal antibody producing hybridoma cells, culturing the hybridoma cells, and isolating monoclonal antibodies from culture.

The invention also provides a method for using an antibody to detect expression of a protein in a sample, the method comprising combining the antibody with a sample under conditions for formation of antibody:protein complexes, and detecting complex formation, wherein complex formation indicates expression of the protein in the sample. In one aspect, the sample is selected from colon, liver, lung, ovary, and prostate. In another aspect, complex formation is compared to standards and is diagnostic of a neoplastic disorder. In a third aspect, the neoplastic disorder is colon or lung cancer.

The invention provides a method for immunopurification of a protein comprising attaching an antibody to a substrate, exposing the antibody to a sample containing protein under conditions to allow antibody:protein complexes to form, dissociating the protein from the complex, and collecting purified protein. The invention also provides a composition comprising an antibody that specifically binds the protein and a labeling moiety or pharmaceutical agent; a kit comprising the composition; an array element comprising the antibody; a substrate upon which the antibody is immobilized. The invention further provides a method for using a antibody to assess efficacy of a molecule or compound, the method comprising treating a sample containing protein with a molecule or compound; contacting the protein in the sample with the antibody under conditions for complex formation; determining the amount of complex formation; and comparing the amount of complex formation in the treated sample with the amount of complex formation in an untreated sample, wherein a difference in complex formation indicates efficacy of the molecule or compound.

The invention provides a method for treating colon cancer comprising administering to a subject in need of therapeutic intervention a therapeutic antibody that specifically binds the protein, a bispecific molecule that specifically binds the protein, and a multispecific molecule that specifically binds the protein, or a composition comprising an antibody and a pharmaceutical agent. The invention also provides a method for delivering a pharmaceutical or therapeutic agent to a cell comprising attaching the pharmaceutical or therapeutic agent to a bispecific molecule that specifically binds the protein and administering the bispecific molecule to a subject in need of therapeutic intervention, wherein the bispecific molecule delivers the pharmaceutical or therapeutic agent to the cell. In one aspect, the cell is an epithelial cell of the colon.

The invention provides an agonist that specifically binds the protein, and a composition comprising the agonist and a pharmaceutical carrier. The invention also provides an antagonist that specifically binds the protein, and a composition comprising the antagonist and a pharmaceutical carrier. The invention further provides a pharmaceutical agent or a small drug molecule that specifically binds the protein.

The invention provides an antisense molecule of 18 to 30 nucleotides in length that specifically binds a portion of a polynucleotide having a nucleic acid sequence of SEQ ID NO:2 or the complement thereof wherein the antisense molecule inhibits expression of the protein encoded by the polynucleotide. The invention also provides an antisense molecule with at least one modified internucleoside linkage or at least one nucleotide analog. The invention further provides that the modified internucleoside linkage is a phosphorothioate linkage and that the modified nucleobase is a 5-methylcytosine.

The invention provides a method for inserting a heterologous marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:2–9, transforming the vector into an embryonic stem cell, selecting a transformed embryonic stem cell, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLES

FIGS. 1A–1D show the amino acid sequence (SEQ ID NO:1) of CTTP encoded by the nucleic acid sequence of SEQ ID NO:2. The alignment was produced using MACDNASIS PRO software (Hitachi Software Engineering, San Bruno Calif.).

Figure 4A:
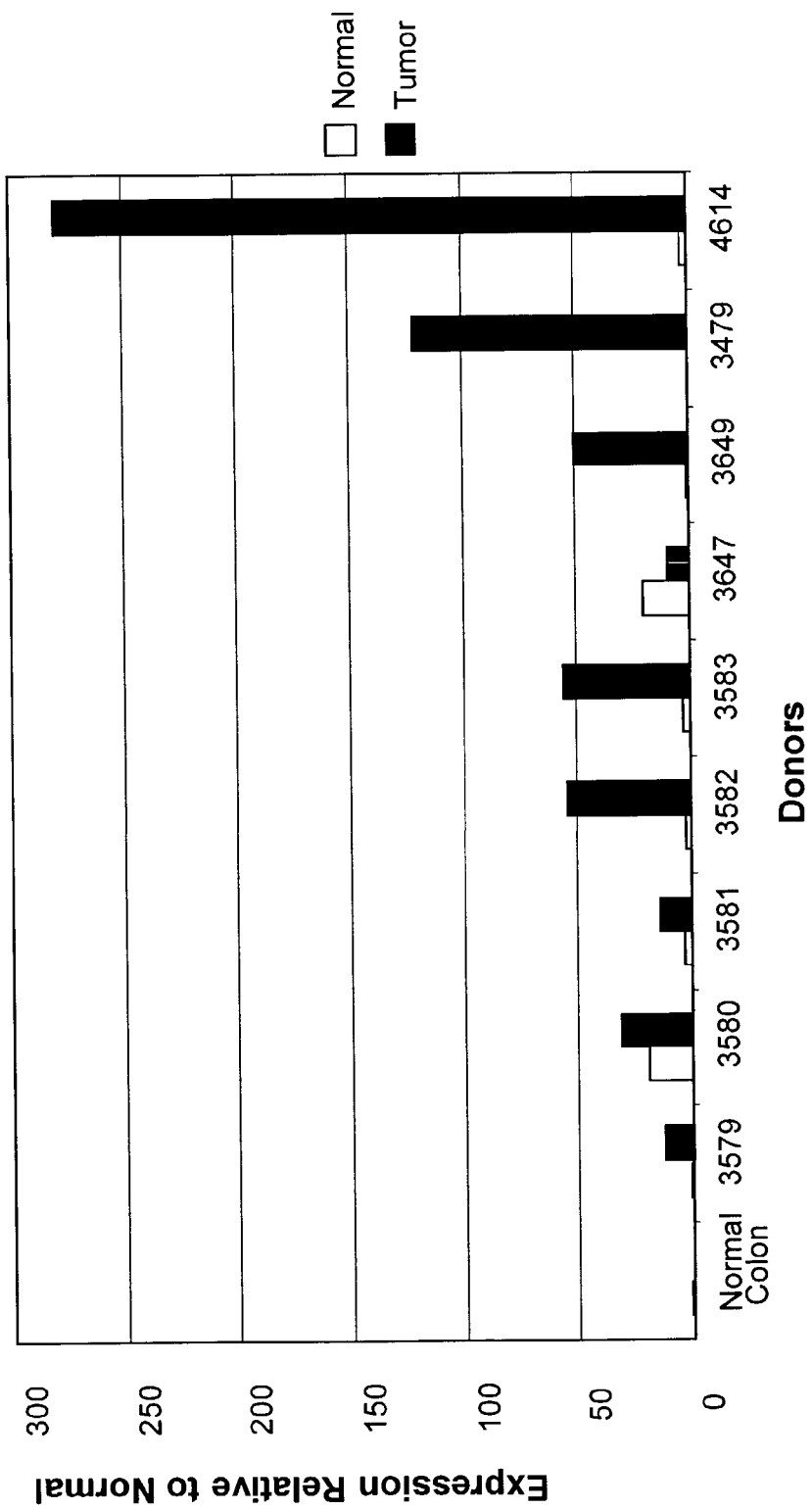
Figure 4B:
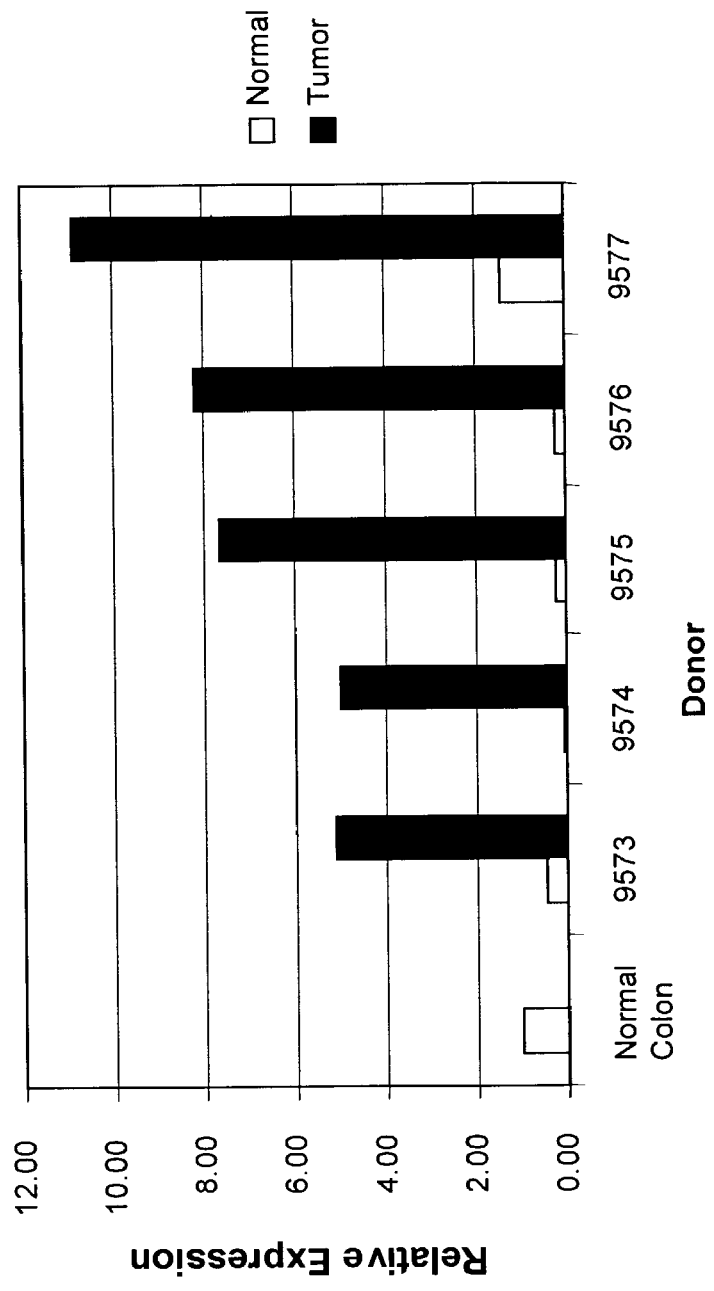

FIGS. 4A and 4B show differential expression of CTTP in 13 out of 14 donor-matched normal/tumor colon samples as determined using the oligonucleotide extending from about nucleotide C512 to about nucleotide G575 of SEQ ID NO:2 and QPCR. FIG. 4A tissues are from Huntsman Cancer Institute (HCI; Salt Lake City Utah); FIG. 4B tissues, from Asterand (Detroit Mich.).

Figure 5:
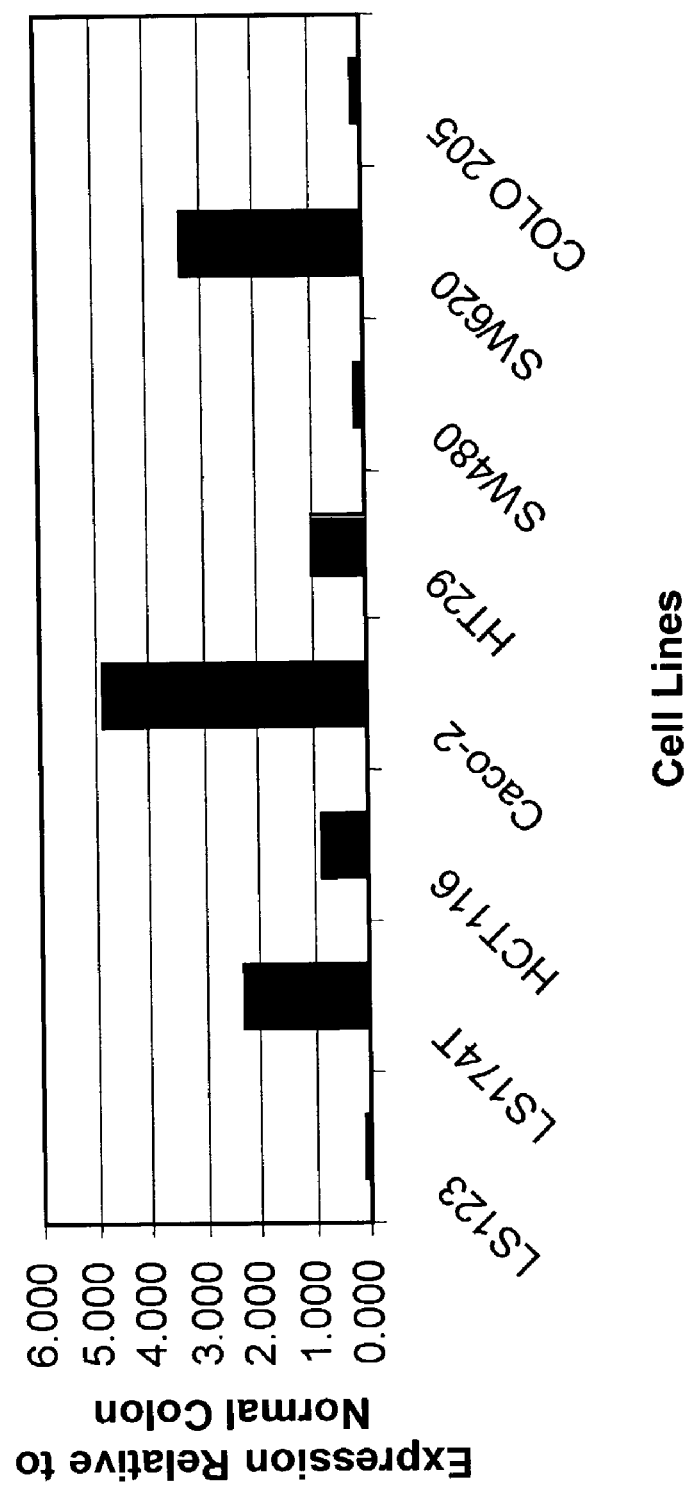

FIG. 5 shows the overexpression of CTTP in colon tumor cell lines relative to a normal colon cell line (LS123) obtained from the ATCC (Manassas Va.) using the oligonucleotide extending from about nucleotide C512 to about nucleotide G575 of SEQ ID NO:2 and QPCR.

Figure 6:
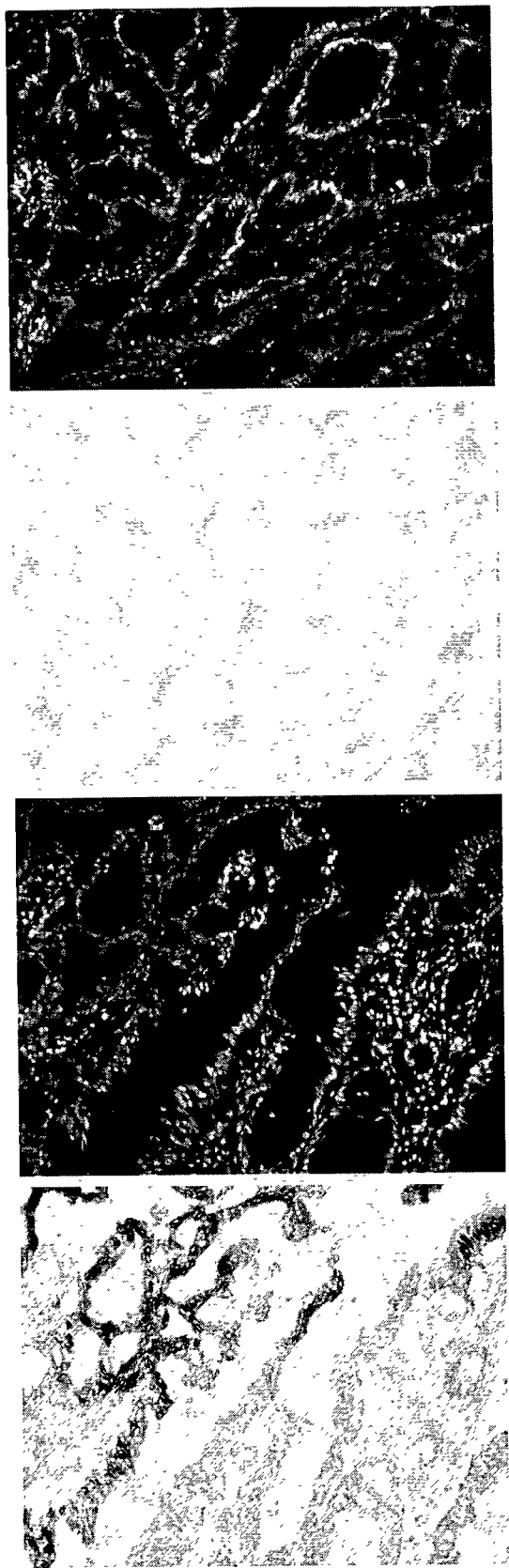

FIG. 6 shows the expression of the transcript encoding CTTP in the epithelial cells of a villous adenocarcinoma. Thin sections were stained with DAPI and hybridized in situ using sense or antisense RNA probes made from a fragment of SEQ ID NO:2 extending from about nucleotide C479 to about nucleotide C847 of SEQ ID NO:2.

Figure 7:
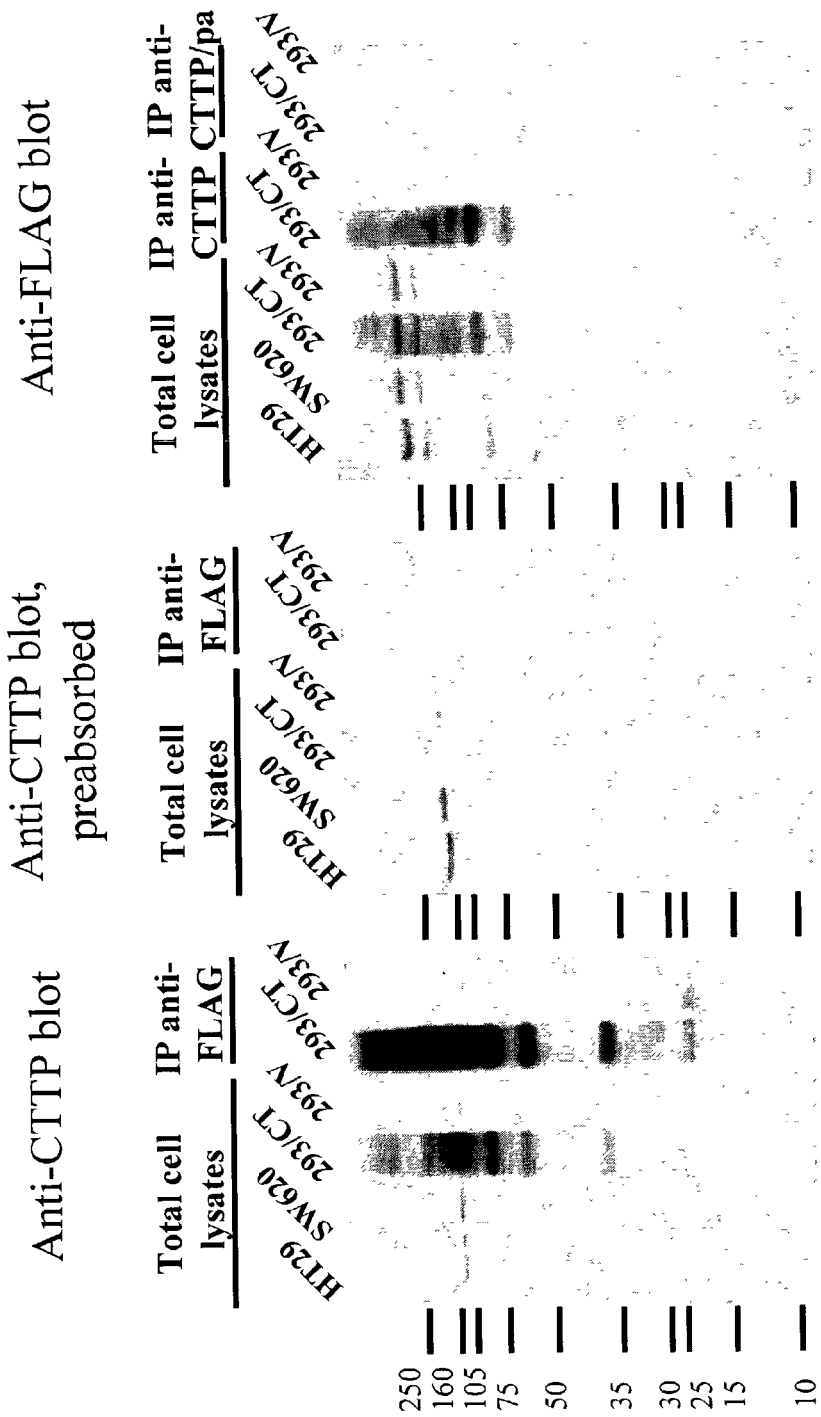

FIG. 7 shows western analyses using two colon cancer cell lines, HT29 and SW620, and 293 cells transfected with a pTRIEX-3 NEO vector alone (293/V, which contains a C-terminal FLAG tag) or a pTRIEX-3 NEO vector containing the cDNA encoding CTTP (293/CT) The three blots were incubated with anti-CT antibody, anti-CT antibody preabsorbed, and IP anti-FLAG antibody, respectively.

Figure 8:
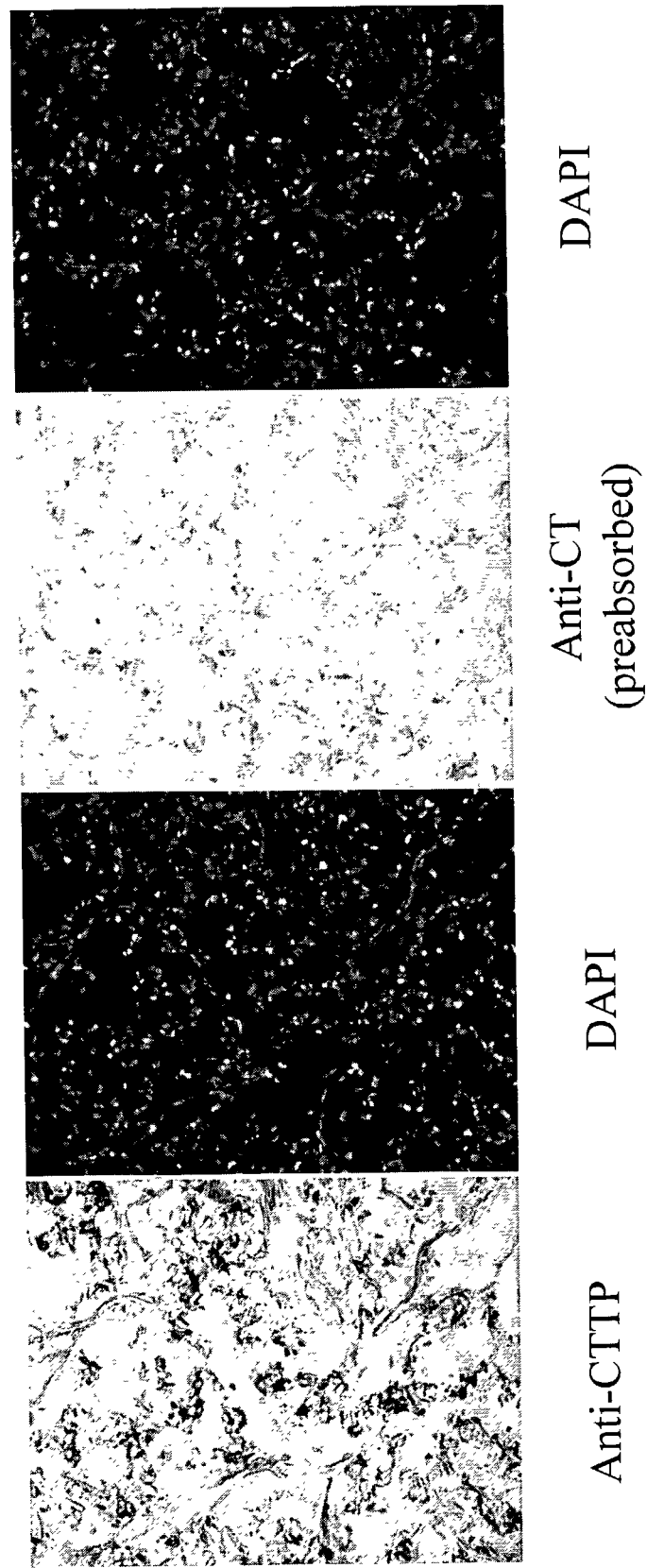

FIG. 8 uses immunohistochemistry and an anti-CT antibody (anti-CT) to show expression of CTTP in thin-sectioned mucinous adenocarcinoma. The section shown in panels 1 and 2 was incubated with anti-CT and counterstained with DAPI. The section shown in panels 3 and 4 was incubated with anti-CT (preabsorbed) and counterstained with DAPI.

Figure 9:
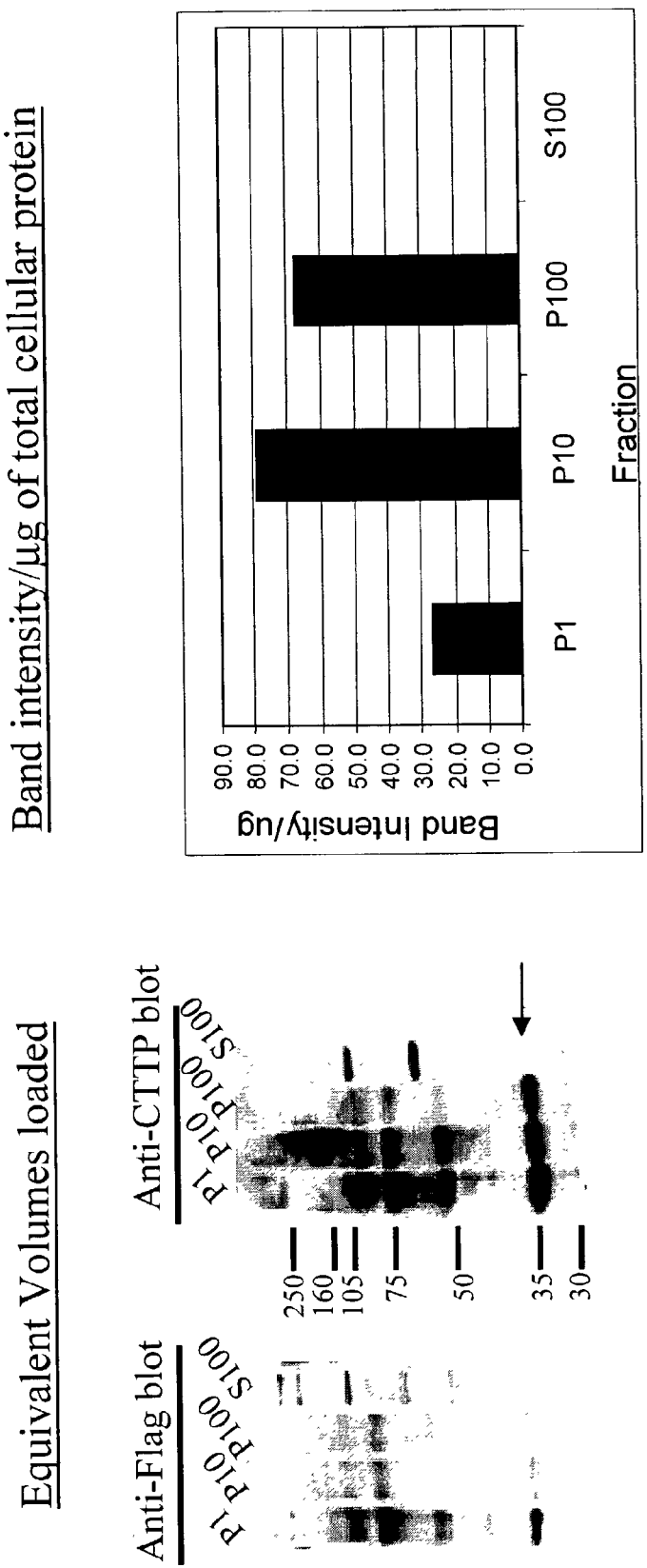
Figure 10:
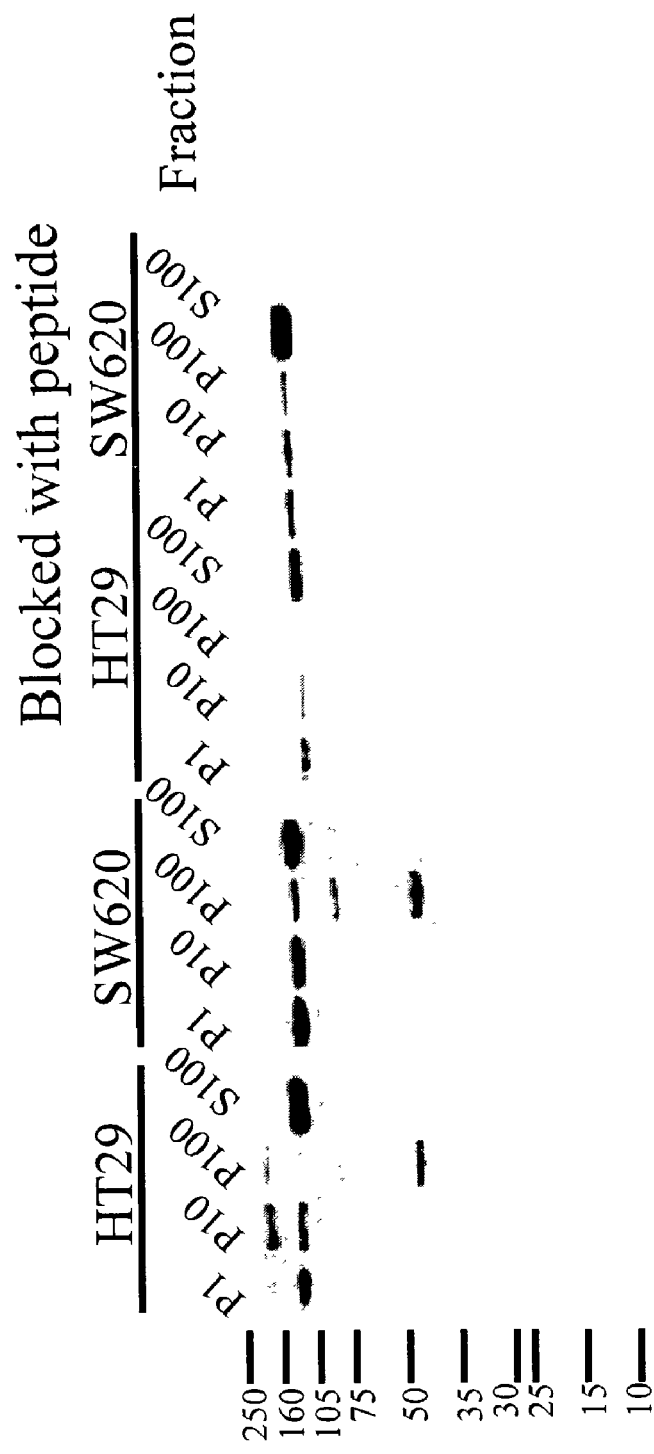

FIGS. 9 and 10 demonstrate fractionation/localization experiments. FIG. 9 used 293 transiently transfected with pTRIEX-3 NEO vector containing the cDNA encoding CTTP (293/CT). Anti-FLAG and anti-CT blots show CTTP expression in the plasma membrane. A graph quantifying the anti-CT bands is displayed for each cellular fraction (nuclear=P1, mitochondrial=P10, plasma membrane=P100, and cytosolic=S100).

FIG. 10 is a western blot showing the distribution of CTTP in fractionated HT29 and SW620 colon cancer cells.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" may include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"Antibody" refers to intact immunoglobulin molecule, a polyclonal antibody, a monoclonal antibody, a chimeric antibody, a recombinant antibody, a humanized antibody, single chain antibodies, a Fab fragment, an F(ab')$_2$ fragment, an Fv fragment, and an antibody-peptide fusion protein.

"Antigenic determinant" refers to an antigenic or immunogenic epitope, structural feature, or region of an oligopeptide, peptide, or protein which is capable of inducing formation of an antibody that specifically binds the protein. Biological activity is not a prerequisite for immunogenicity.

"Array" refers to an ordered arrangement of at least two cDNAs, proteins, or antibodies on a substrate. At least one of the cDNAs, proteins, or antibodies represents a control or standard, and the other cDNA, protein, or antibody is of diagnostic or therapeutic interest. The arrangement of at least two and up to about 40,000 cDNAs, proteins, or antibodies on the substrate assures that the size and signal intensity of each labeled complex, formed between each cDNA and at least one nucleic acid, each protein and at least one ligand or antibody, or each antibody and at least one protein to which the antibody specifically binds, is individually distinguishable.

A "bispecific molecule" has two different binding specificities and can be bound to two different molecules or two different sites on a molecule concurrently. Similarly, a "multispecific molecule" can bind to multiple (more than two) distinct targets, one of which is a molecule on the surface of an immune cell. Antibodies can perform as or be a part of bispecific or multispecific molecules.

"CTTP" refers to a transmembrane protein that is exact or highly homologous (>85%) to the amino acid sequence of SEQ ID NO:1 obtained from any species including bovine, ovine, porcine, murine, equine, and preferably the human species, and from any source, whether natural, synthetic, semi-synthetic, or recombinant.

The "complement" of a cDNA of the Sequence Listing refers to a nucleic acid molecule which is completely complementary over its full length and which will hybridize to a nucleic acid molecule under conditions of high stringency.

"cDNA" refers to an isolated polynucleotide, nucleic acid molecule, or any fragment thereof that contains from about 400 to about 12,000 nucleotides. It may have originated recombinantly or synthetically, may be double-stranded or single-stranded, may represent coding and noncoding 3' or 5' sequence, and generally lacks introns.

The phrase "cDNA encoding a protein" refers to a nucleic acid whose sequence closely aligns with sequences that encode conserved regions, motifs or domains identified by employing analyses well known in the art. These analyses include BLAST (Basic Local Alignment Search Tool; Altschul (1993) J Mol Evol 36:290–300; Altschul et al. (1990) J Mol Biol 215:403–410) and BLAST2 (Altschul et al. (1997) Nucleic Acids Res 25:3389–3402) which provide identity within the conserved region. Brenner et al. (1998; Proc Natl Acad Sci 95:6073–6078) who analyzed BLAST for its ability to identify structural homologs by sequence identity found 30% identity is a reliable threshold for sequence alignments of at least 150 residues and 40% is a reasonable threshold for alignments of at least 70 residues (Brenner, page 6076, column 2).

A "composition" refers to the polynucleotide and a labeling moiety; a purified protein and a pharmaceutical carrier or a heterologous, labeling or purification moiety; an antibody and a labeling moiety or pharmaceutical agent; and the like.

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a cDNA or a protein can also involve the replacement of a hydrogen by an acetyl, acyl, alkyl, amino, formyl, or morpholino group (for example, 5-methylcytosine). Derivative molecules retain the biological activities of the naturally occurring molecules but may confer longer lifespan or enhanced activity.

"Differential expression" refers to an increased or upregulated or a decreased or downregulated expression as detected by absence, presence, or at least two-fold change in the amount of transcribed messenger RNA or translated protein in a sample.

"Disorder" refers to conditions, diseases or syndromes in which CTTP or the mRNA encoding CTTP are differentially expressed; these include neoplastic disorders such as cancers of the colon, liver, ovary, and prostate.

An "expression profile" is a representation of gene expression in a sample. A nucleic acid expression profile is produced using sequencing, hybridization, or amplification technologies and mRNAs or cDNAs from a sample. A protein expression profile, although time delayed, mirrors the nucleic acid expression profile and uses two-dimensional polyacrylamide electrophoresis (2D-PAGE), mass spectrophotometry (MS), enzyme-linked immunosorbent assays (ELISAs), fluorescence activated cell sorting (FACS), radioimmunoassays (RIAs), scintillation counters, and or arrays and antibodies and labeling moieties to detect protein expression in a sample. The nucleic acids, proteins, or antibodies may be used in solution or attached to a substrate, and their detection is based on methods and labeling moieties well known in the art.

"Fragment" refers to a chain of consecutive nucleotides from about 50 to about 4000 base pairs in length. Fragments may be used in PCR or hybridization technologies to identify related nucleic acid molecules and in binding assays to screen for a ligand. Such ligands are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. Hybridization conditions, degree of complementarity and the use of nucleotide analogs affect the efficiency and stringency of hybridization reactions.

"Identity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197), CLUSTALW (Thompson et al. (1994) Nucleic Acids Res 22:4673–4680), or BLAST2 (Altschul (1997, supra). BLAST2 may be used in a standardized and reproducible way to insert gaps in one of the sequences in order to optimize alignment and to achieve a more meaningful comparison between them. "Similarity" uses the same algorithms but takes conservative substitution of residues into account. In proteins, similarity exceeds identity in that substitution of a valine for a leucine or isoleucine, is counted in calculating the reported percentage. Substitutions which are considered to be conservative are well known in the art.

"Isolated" or "purified" refers to any molecule or compound that is separated from its natural environment and is from about 60% free to about 90% free from other components with which it is naturally associated.

"Labeling moiety" refers to any reporter molecule including radionuclides, enzymes, fluorescent, chemiluminescent, or chromogenic agents, substrates, cofactors, inhibitors, or magnetic particles than can be attached to or incorporated into a polynucleotide, protein, or antibody. Visible labels and dyes include but are not limited to anthocyanins, β glucuronidase, BIODIPY, Coomassie blue, Cy3 and Cy5, DAPI, digoxigenin, fluorescein, FITC, gold, green fluorescent protein, lissamine, luciferase, phycoerythrin, rhodamine, spyro red, silver, and the like. Radioactive markers include radioactive forms of hydrogen, iodine, phosphorous, sulfur, and the like.

"Ligand" refers to any agent, molecule, or compound which will bind specifically to a polynucleotide or to an epitope of a protein. Such ligands stabilize or modulate the activity of polynucleotides or proteins and may be composed of inorganic and/or organic substances including minerals, cofactors, nucleic acids, proteins, carbohydrates, fats, and lipids.

"Oligonucleotide" refers a single-stranded molecule from about 18 to about 60 nucleotides in length which may be used in hybridization or amplification technologies or in regulation of replication, transcription or translation. Equivalent terms are amplicon, amplimer, primer, and oligomer.

A "pharmaceutical agent" may be an antibody, an antisense molecule, a bispecific molecule, a multispecific molecule, a protein, a radionuclide, a small drug molecule, a cytotoxin such as vincristine, vinblastine, cisplatin, doxorubicin, or methotrexate, or any combination of these elements.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single-stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic determinant of the protein identified using Kate-Doolittle algorithms of the PROTEAN program (DNAS-TAR, Madison Wis.). An "oligopeptide" is an amino acid sequence from about five residues to about 15 residues that is used as part of a fusion protein to produce an antibody.

"Sample" is used in its broadest sense as containing nucleic acids, proteins, and antibodies. A sample may comprise a bodily fluid such as ascites, blood, cerebrospinal fluid, lymph, semen, sputum, urine and the like; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue, a tissue biopsy, or a tissue print; buccal cells, skin, hair, a hair follicle; and the like.

"Specific binding" refers to a precise interaction between two molecules which is dependent upon their structure, particularly their molecular side groups. For example, the intercalation of a regulatory protein into the major groove of a DNA molecule or the binding between an epitope of a protein and an agonist, antagonist, or antibody.

"Substrate" refers to any rigid or semi-rigid support to which polynucleotides, proteins, or antibodies are bound and includes magnetic or nonmagnetic beads, capillaries or other tubing, chips, fibers, filters, gels, membranes, plates, polymers, slides, wafers, and microparticles with a variety of surface forms including channels, columns, pins, pores, trenches, and wells.

A "transcript image" (TI) is a profile of gene transcription activity in a particular tissue at a particular time. TI provides assessment of the relative abundance of expressed polynucleotides in the cDNA libraries of an EST database as described in U.S. Pat. No. 5,840,484, incorporated herein by reference.

"Variant" refers to molecules that are recognized variations of a protein or the polynucleotides that encode it. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

The Invention

The invention is based on the discovery of a transmembrane protein (CTTP), its encoding cDNA, and an antibody that specifically binds the protein and on their use in the characterization, diagnosis, prognosis, treatment and evaluation of treatment of a neoplastic disorder and in particular colon and lung cancers. PCT international application No. PCT/US00/07817, filed Mar. 22, 2000 is incorporated in its entirely by reference herein.

A cDNA encoding CTTP of the present invention was first identified in Incyte clone 4901066 from the prostate cDNA library (OVARDIT01) using a computer search for amino acid sequence alignments. The full length sequence, SEQ ID NO:2, was derived from Incyte clones 1752794F6 (LIVRTUT01), 3221661CA2 (COLNNON03), 3221661R6 (COLNNON03), SBQA03652D1, and SBQA04510D1 which are SEQ ID NOs:3–7, respectively. Incyte clone 3221661CA2 been designated a verified reagent; and SEQ ID NO:2 is represented on microarrays. Useful fragments of SEQ ID NO:2 include the cDNAs of SEQ ID NOs:3–7; a fragment from about nucleotide C479 to about nucleotide C847 of SEQ ID NO:2, and fragments which encode extramembrane binding domains of the protein extending from about nucleotide G1 to about nucleotide T332, from about nucleotide G500 to about nucleotide G792, and from about nucleotide G1083 to about nucleotide G1226 of SEQ ID NO:2. An oligonucleotide for QPCR analysis extends from about C512 to about G575 on SEQ ID NO:2.

Figure 2:
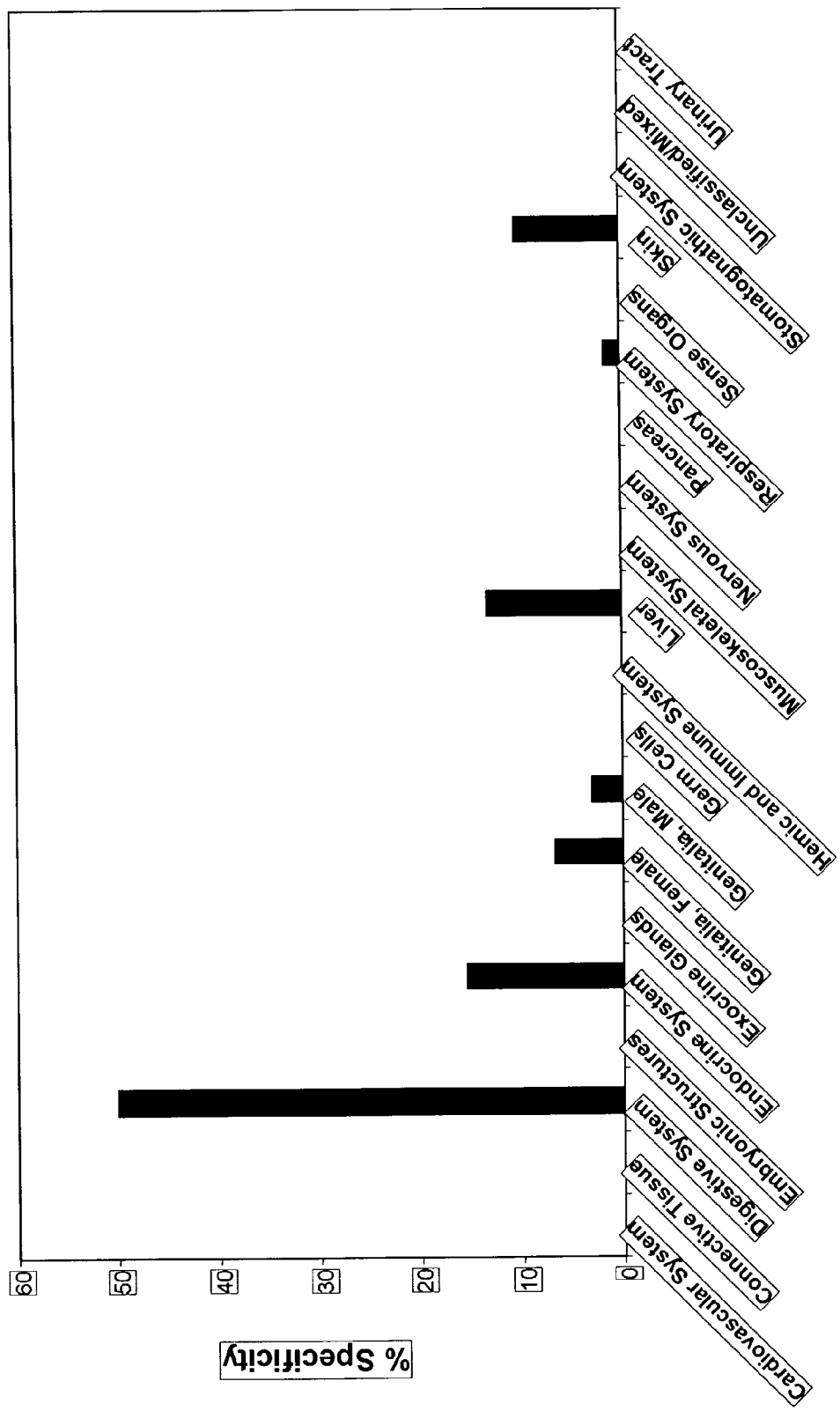
FIG. 2 shows the distribution of transcripts encoding CTTP in the LIFESEQ Gold database (Incyte Genomics, Palo Alto Calif.) by category. The distribution is based on clone counting, and the categories are listed in EXAMPLE V under Transcript Imaging.

Northern analysis showed expression of this sequence in cancerous tissues (56%) diseased tissues (24%) and in proliferating cells (12%). FIG. 2 shows the distribution of transcripts encoding CTTP in the LIFESEQ Gold database (Incyte Genomics) by tissue category. The distribution is based on clone counting, and the categories are identical to those listed in EXAMLE V under transcript imaging. As can be seen on the graph, about 50% of transcript expression is in the digestive system.

In one embodiment, the invention encompasses a protein comprising a polypeptide having the amino acid sequence of SEQ ID NO:1 as shown in FIGS. 1A–1D. CTTP is 320 amino acids in length, has a predicted molecular weight of 34.7 kDa, and has three potential N glycosylation sites at N84, N109, and N121, and six potential phosphorylation sites at S86, T96, T131, Y156, T280, and S285. A signal sequence extends from about residue M1 to about residue V22. Topology mapping suggests that CTTP has five transmembrane spanning motifs that extend from about P23 to about 145, from about F52 to about F72, from about A176 to about L198, from about L208 to about I227, and from about L254 to about Y272. An oligopeptide extending from about residue D125 to about residue A140 of SEQ ID NO:1 has high immunogenicity and was used as an antigenic determinant to produce polyclonal antibodies. Useful biologically active portions of the protein selected from about residue M1 to about residue V22, from about S73 to about L175, and from about residue V273 to about residue I320 of SEQ ID NO:1

Microarray data first showed that SEQ ID NO:2 was preferentially and differentially expressed in neoplastic disorders, and this discovery led to further studies including QPCR, production of an antibody that specifically binds CTTP, in situ hybridization, immunohistochemistry, and western analysis to localize the protein in transfected 293 cells and in HT29 and SW620 colon cancer cells.

Figure 3:
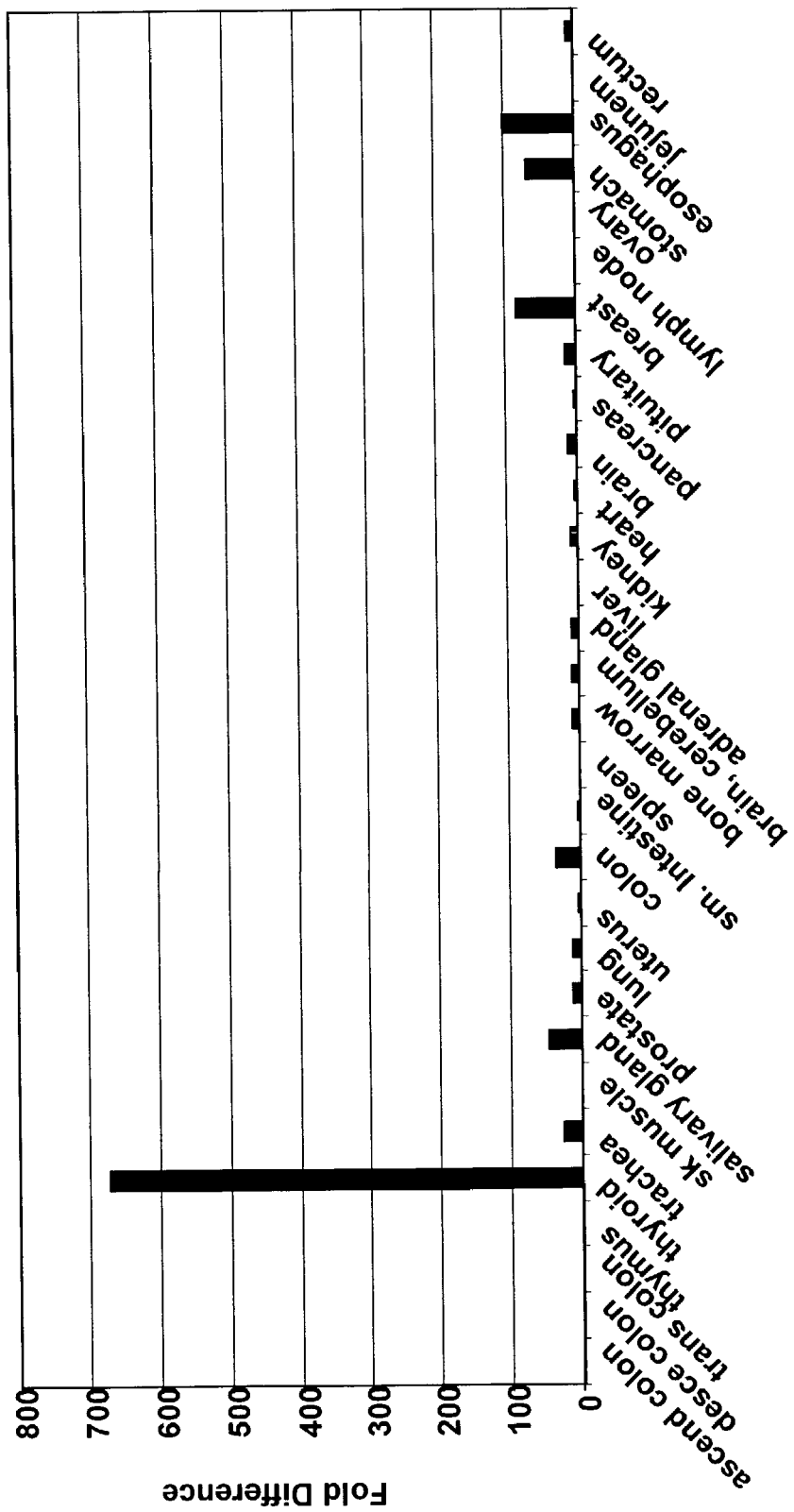
FIG. 3 shows fold differences in expression of CTTP as detected using the oligonucleotide extending from about nucleotide C512 to about nucleotide G575 of SEQ ID NO:2 in normal tissues obtained from Clontech (Palo Alto Calif.) and Clinomics (Pittsfield Mass.) as determined using quantitative PCR (QPCR).

The results of QPCR experiments using the oligonucleotide that extends from about C512 to about G575 on SEQ ID NO:2 are shown in FIGS. 3–5. FIG. 3 shows that the normal expression of CTTP is highest in thyroid tissue with decreasingly lower levels seen in esophagus, breast, stomach, salivary gland, colon, prostate, trachea, pituitary, prostate, brain, lung, and adrenal gland, respectively. The transcript was not expressed in peripheral blood leukocytes (data not shown). FIGS. 4A and 4B show differential expression of CTTP in 13 out of 14 donor-matched normal/tumor colon samples. The colon tumors shown in FIG. 4A were obtained from HCI; and in FIG. 4B, from Asterand; these tissues are described in EXAMPLE VII.

FIG. 5 shows the overexpression of CTTP in colon tumor cell lines relative to normal colon, LS123, using the oligonucleotide extending from about C512 to about G575 on SEQ ID NO:2 as determined by QPCR. The cell lines were obtained from the ATCC. The last two cell lines, SW620 and COLO 205, are metastases of colon carcinoma derived from ascitic-fluid and lymph node tissue, respectively.

FIG. 6 shows expression of the transcript encoding CTTP in the epithelial cells of a colon cancer. Transcript expression was visualized using in situ hybridization in a thin-sectioned villous adenocarcinoma sample (Donor ID 8306, Asterand) using sense or antisense RNA probes made from a fragment extending from about nucleotide C479 to about nucleotide C847 of SEQ ID NO:2. For contrast, the respective sections were counterstained with DAPI.

FIG. 7 shows western analyses using two colon cancer cell lines, HT29 and SW620, and 293 cells transfected with a with a pTRIEX-3 NEO vector alone (293/V which has a C-terminal FLAG tag) or a with a pTRIEX-3 NEO vector containing the cDNA encoding CTTP (293/CT). In FIG. 7, three blots have been incubated with anti-CT, anti-CT preabsorbed, and anti-FLAG antibody, respectively. IP is the abbreviation for immunoprecipitated. A 16 amino-acid oligopeptide which extends from residue D110 to residue A124 of SEQ ID NO:1 which was synthesized and conjugated to KLH (Sigma-Aldrich, St. Louis Mo.) by SynPep (Dublin Calif.). Covance (Princeton N.J.) used the conjugated oligopeptide to immunize rabbits and produce the anti-CT antibody. Anti-CT recognizes a 35 kDa protein in the 293/CT extract which represents the monomeric molecular weight of CTTP and also binds to species with approximate molecular weights of 70 kDa, 105 kDa, and 150 kDa. These species are not detected when the anti-CT is pre-incubated with the oligopeptide or CTTP (preabsorbed); therefore, these species are specific to and likely to contain CTTP. Given that the labeled species closely resemble multimers, it is likely that CTTP forms complexes in the membrane with itself or other membrane proteins.

FIG. 8 uses immunohistochemistry and anti-CT to show expression of CTTP in thin-sectioned mucinous adenocarcinoma (Donor ID 9697, NCI Cooperative Human Tissue Network, Bethesda Md.). The section shown in panels 1 and 2 was incubated with anti-CT and counterstained with DAPI. CTTP is clearly expressed in panel 1. The section shown in panels 3 and 4, incubated with anti-CT (preabsorbed) and counterstained with DAPI does not show expression.

FIG. 9 shows fractionation/localization experiments using transfected 293/CT cells. The cells were fractionated into nuclear (P1), mitochondrial (P10), plasma membrane (P100), and cytosolic (S100) fractions, then the pellets were resuspended in equivalent volumes of loading buffer, loaded on 4–12% gradient denaturing polyacrylamide gel, separated by electrophoresis, and transferred to a polyvinylidene difluoride (PVDF) membrane. Comparison of the anti-FLAG and anti-CT blots shows that CTTP is expressed in cell membranes. The results, band intensity/microgram of total cellular protein, are also displayed graphically for each fraction.

FIG. 10 shows the distribution of CTTP in fractionated HT29 and SW620 colon cancer cells. Comparison of the control (blocked with peptide) and normal blot shows CTTP is primarily localized to the plasma membrane, P100 fraction, of these cell lines.

Immunohistochemistry experiments compared the expression of CTTP in thin-sectioned preparations. Expression in mucinous adenocarcinoma cells (FIG. 9) was greater than that seen in villous adenocarcinoma cells (not shown, Donor ID 8306, Asterand) which was, in turn, greater than that seen in normal colon epithelial cells (not shown; Donor ID 8403, Asterand). CTTP is overexpressed in the epithelium of colon tumors.

The significant differential expression of CTTP between tumor and normal lung samples is shown in the table below. The first column shows the $\log_2$ value; the second column, the tumor donor (Dn) ID; the third column, the description of the lung tumor; and the fourth column, the normal donor ID. These experiments were done using the HumanGenome GEM3 microarray and values greater than two-fold (log$_2$>1.0) were considere significant. In contrast to colon cancer, the expression of CTTP and the nucleic acids encoding CTTP in lung were downregulated.

| log2(Cy3/Cy5) | Tumor Dn ID | Description of Lung Tumor | Normal Dn ID |
|---|---|---|---|
| −1.20231 | 7186 | Tumor, right middle lobe, atypical lung cancer | Pool |
| −1.27601 | 7192 | Tumor, right upper lobe, large cell carcinoma | 8310 |
| −1.11548 | 7976 | Tumor, Non-Small Cell Lung | 9007 |
| −1.1315 | 7164 | Tumor, carcinoid | 7164 |

Mammalian variants of the cDNA encoding CTTP were identified using BLAST2 with default parameters and the ZOOSEQ databases (Incyte Genomics). These highly homologous cDNAs have about 85% identity to all or part of the cDNA encoding the human protein as shown in the, table below. The first column represents the SEQ ID NO: for homologous cDNAs (SEQ ID$_{Var}$); the second column, the Incyte ID for the homologous cDNAs (Incyte ID$_{Var}$); the third column, the species; the fourth column, the percent identity to the human cDNA; and the fifth column, the nucleotide alignment of the homologous cDNA to the human cDNA.

| SEQ ID$_{Var}$ | Incyte ID$_{Var}$ | Species | Identity | Nt$_H$ Alignment |
|---|---|---|---|---|
| 8 | 224394_Rn.1 | Rat | 84% | 219–351 |
| 9 | 093983_Mm.1 | Mouse | 86% | 412–1394 |

It will be appreciated by those skilled in the art that as a result of the degeneracy of the genetic code, a multitude of cDNAs encoding CTTP, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring CTTP, and all such variations are to be considered as being specifically disclosed.

The cDNAs of SEQ ID NOs:2–9 may be used in hybridization, amplification, and screening technologies to identify and distinguish among SEQ ID NO:2 and related molecules in a sample. The mammalian cDNAs, SEQ ID NOs:8 and 9, may be used to produce transgenic cell lines or organisms which are model systems for human colon or lung cancers and upon which the toxicity and efficacy of therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention cDNA Libraries

In a particular embodiment disclosed herein, mRNA is isolated from mammalian cells and tissues using methods which are well known to those skilled in the art and used to prepare the cDNA libraries. The Incyte cDNAs were isolated from mammalian cDNA libraries prepared as described in the EXAMPLES. The consensus sequence is present in a single clone insert ,or chemically assembled, based on the electronic assembly from sequenced fragments including Incyte cDNAs and extension and/or shotgun sequences. Computer programs, such as PHRAP (P Green, University of Washington, Seattle Wash.) and the AUTOASSEMBLER application (ABI), are used in sequence assembly and are described in EXAMPLE V. After verification of the 5' and 3' sequence, at least one representative cDNA which encodes CTTP is designated a reagent for research and development.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Biosciences (APB), Piscataway N.J.), or combinations of polymerases and proofreading exonucleases (Invitrogen, Carlsbad Calif.). Sequence preparation is automated with machines such as the MICROLAB 2200 system (Hamilton, Reno Nev.) and the DNA ENGINE thermal cycler (MJ Research, Watertown Mass.) and sequencing, with the PRISM 3700, 377 or 373 DNA sequencing systems (ABI) or the MEGABACE 1000 DNA sequencing system (APB).

The nucleic acid sequences of the cDNAs presented in the Sequence Listing were prepared by such automated methods and may contain occasional sequencing errors and unidentified nucleotides, designated with an N, that reflect state-of-the-art technology at the time the cDNA was sequenced. Vector, linker, and polyA sequences were masked using algorithms and programs based on BLAST, dynamic programming, and dinucleotide nearest neighbor analysis. Ns and SNPs can be verified either by resequencing the cDNA or using algorithms to compare multiple sequences that overlap the area in which the Ns or SNP occur. Both of these techniques are well known to and used by those skilled in the art. The sequences may be analyzed using a variety of algorithms described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences, including vector or chimeric sequences, can be removed, and deleted sequences can be restored to complete the assembled, finished sequences.

Extension of a Nucleic Acid Sequence

The sequences of the invention may be extended using various PCR-based methods known in the art. For example, the XL-PCR kit (ABI), nested primers, and cDNA or genomic DNA libraries may be used to extend the nucleic acid sequence. For all PCR-based methods, primers may be designed using software, such as OLIGO primer analysis software (Molecular Biology Insights, Cascade CO) to be about 22 to 30 nucleotides in length, to have a GC content of about 50% or more, and to anneal to a target molecule at temperatures from about 55C. to about 68C. When extending a sequence to recover regulatory elements, genomic, rather than cDNA libraries are used.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the CTTP, allelic variants, or related molecules. The probe may be DNA or RNA, may be single-stranded, and should have at least 50% sequence identity to any of the nucleic acid sequences, SEQ ID NOs:2–9. Hybridization probes may be produced using oligolabeling, nick-translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using kits such as those provided by APB.

The stringency of hybridization is determined by G+C content of the probe, salt concentration, and temperature. In particular, stringency can be increased by reducing the concentration of salt or raising the hybridization temperature. Hybridization can be performed at low stringency with buffers, such as 5×SSC with 1% sodium dodecyl sulfate (SDS) at 60C., which permits the formation of a hybridization complex between nucleic acid sequences that contain some mismatches. Subsequent washes are performed at higher stringency with buffers such as 0.2×SSC with 0.1% SDS at either 45C. (medium stringency) or 68C. (high stringency). At high stringency, hybridization complexes will remain stable only where the nucleic acids are completely complementary. In some membrane-based hybridizations, from about 35% to about 50% formamide can be added to the hybridization solution to reduce the temperature at which hybridization is performed. Background signals can be reduced by the use of detergents such as Sarkosyl or TRITON X-100 (Sigma-Aldrich) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods well known in the art. Oligonucleotides or cDNAs may be used as hybridization probes or targets to monitor the expression level of large numbers of genes simultaneously or to identify genetic variants, mutations, and single nucleotide polymorphisms. Arrays may be used to determine gene function; to understand the genetic basis of a condition, disease, or disorder; to diagnose a condition, disease, or disorder; and to develop and monitor the activities of therapeutic agents. (See, e.g., U.S. Pat. No. 5,474,796; Schena et al. (1996) Proc Natl Acad Sci 93:10614–10619; Heller et al. (1997) Proc Natl Acad Sci 94:2150–2155; U.S. Pat. No. 5,605,662.)

Hybridization probes are also useful in mapping the naturally occurring genomic sequence. The probes may be hybridized to a particular chromosome, a specific region of a chromosome, or an artificial chromosome construction. Such constructions include human artificial chromosomes, yeast artificial chromosomes, bacterial artificial chromosomes, bacterial P1 constructions, or the cDNAs of libraries made from single chromosomes.

QPCR

QPCR is a method for quantifying a nucleic acid molecule based on detection of a fluorescent signal produced during PCR amplification (Gibson et al. (1996) Genome Res 6:995–1001; Heid et al. (1996) Genome Res 6:986–994). Amplification is carried out on machines such as the PRISM 7700 detection system (ABI) which consists of a 96-well thermal cycler connected to a laser and charge-coupled device (CCD) optics system. To perform QPCR, a PCR reaction is carried out in the presence of a doubly labeled probe. The probe, which is designed to anneal between the standard forward and reverse PCR primers, is labeled at the 5' end by a flourogenic reporter dye such as 6-carboxyfluorescein (6-FAM) and at the 3' end by a quencher molecule such as 6-carboxy-tetramethyl-rhodamine (TAMRA). As long as the probe is intact, the 3' quencher extinguishes fluorescence by the 5' reporter. However, during each primer extension cycle, the annealed probe is degraded as a result of the intrinsic 5' to 3' nuclease activity of Taq polymerase (Holland et al. (1991) Proc Natl Acad Sci 88:7276–7280). This degradation separates the reporter from the quencher, and fluorescence is detected every few seconds by the CCD. The higher the starting copy number of the nucleic acid, the sooner an increase in fluorescence is observed. A cycle threshold ($C_T$) value, representing the cycle number at which the PCR product crosses a fixed threshold of detection is determined by the instrument software. The $C_T$ is inversely proportional to the copy number of the template and can therefore be used to calculate either the relative or absolute initial concentration of the nucleic acid molecule in the sample. The relative concentration of two different molecules can be calculated by determining their respective $C_T$ values (comparative $C_T$ method). Alternatively, the absolute concentration of the nucleic acid molecule can be calculated by constructing a standard curve using a housekeeping molecule of known concentration. The process of calculating $C_T$ values, preparing a standard curve, and determining starting copy number is performed using SEQUENCE DETECTOR 1.7 software (ABI).

Expression

Any one of a multitude of cDNAs encoding CTTP may be cloned into a vector and used to express the protein, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors or plant cell systems transformed with expression vectors containing viral and/or bacterial elements (Ausubel supra, unit 16). In mammalian cell systems, an adenovirus transcriptional/ translational complex may be utilized. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional pBLUESCRIPT vector (Stratagene, La Jolla Calif.) or pSPORT1 plasmid (Invitrogen). Introduction of a nucleic acid sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers may be propagated using culture techniques. Visible markers are also used to estimate the amount of protein expressed by the introduced genes. Verification that the host cell contains the desired cDNA is based on DNA-DNA or DNA-RNA hybridizations or PCR amplification.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6×His, FLAG, MYC, and the like. GST and 6-His are purified using affinity matrices such as immobilized glutathione and metal-chelate resins, respectively. FLAG and MYC are purified using monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16).

Protein Identification

Several techniques have been developed which permit rapid identification of proteins using high performance liquid chromatography and mass spectrometry (MS). Beginning with a sample containing proteins, the method is:1) proteins are separated using two-dimensional gel electrophoresis (2-DE), 2) selected proteins are excised from the gel and digested with a protease to produce a set of peptides; and 3) the peptides are subjected to mass spectral analysis to derive peptide ion mass and spectral pattern information. The MS information is used to identify the protein by comparing it with information in a protein database (Shevenko et al. (1996) Proc Natl Acad Sci 93:14440–14445).

Proteins are separated by 2DE employing isoelectric focusing (IEF) in the first dimension followed by SDS-PAGE in the second dimension. For IEF, an immobilized pH gradient strip is useful to increase reproducibility and resolution of the separation. Alternative techniques may be used to improve resolution of very basic, hydrophobic, or high molecular weight proteins. The separated proteins are detected using a stain or dye such as silver stain, Coomassie blue, or spyro red (Molecular Probes, Eugene OR) that is compatible with MS. Gels may be blotted onto a PVDF membrane for western analysis and optically scanned using a STORM scanner (APB) to produce a computer-readable output which is analyzed by pattern recognition software such as MELANIE (GeneBio, Geneva, Switzerland). The software annotates individual spots by assigning a unique identifier and calculating their respective x,y coordinates, molecular masses, isoelectric points, and signal intensity. Individual spots of interest, such as those representing differentially expressed proteins, are excised and proteolytically digested with a site-specific protease such as trypsin or chymotrypsin, singly or in combination, to generate a set of small peptides, preferably in the range of 1–2 kDa. Prior to digestion, samples may be treated with reducing and alkylating agents, and following digestion, the peptides are then separated by liquid chromatography or capillary electrophoresis and analyzed using MS.

MS converts components of a sample into gaseous ions, separates the ions based on their mass-to-charge ratio, and determines relative abundance. For peptide mass fingerprinting analysis, a MALDI-TOF (Matrix Assisted Laser Desorption/Ionization-Time of Flight), ESI (Electrospray Ionization), and TOF-TOF (Time of Flight/Time of Flight) machines are used to determine a set of highly accurate peptide masses. Using analytical programs, such as TURBOSEQUEST software (Finnigan, San Jose Calif.), the MS data is compared against a database of theoretical MS data derived from known or predicted proteins. A minimum match of three peptide masses is used for reliable protein identification. If additional information is needed for identification, Tandem-MS may be used to derive information about individual peptides. In tandem-MS, a first stage of MS is performed to determine individual peptide masses. Then selected peptide ions are subjected to fragmentation using a technique such as collision induced dissociation (CID) to produce an ion series. The resulting fragmentation ions are analyzed in a second round of MS, and their spectral pattern may be used to determine a short stretch of amino acid sequence (Dancik et al. (1999) J Comput Biol 6:327–342).

Assuming the protein is represented in the database, a combination of peptide mass and fragmentation data, together with the calculated MW and pI of the protein, will usually yield an unambiguous identification. If no match is found, protein sequence can be obtained using direct chemical sequencing procedures well known in the art (cf. Creighton (1984) *Proteins, Structures and Molecular Properties*, WH Freeman, New York N.Y.).

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the 431A peptide synthesizer (ABI). A protein or portion thereof may be purified by preparative high performance liquid chromatography and its composition confirmed by amino acid analysis or by sequencing (Creighton (1984) *Proteins, Structures and Molecular Properties*, WH Freeman, New York N.Y.).

Antibodies

Antibodies, or immunoglobulins (Ig), are components of immune response expressed on the surface of or secreted into the circulation by B cells. The prototypical antibody is a tetramer composed of two identical heavy polypeptide chains (H-chains) and two identical light polypeptide chains (L-chains) interlinked by disulfide bonds which binds and neutralizes foreign antigens. Based on their H-chain, antibodies are classified as IgA, IgD, IgE, IgG or IgM. The most common class, IgG, is tetrameric while other classes are variants or multimers of the basic structure.

Antibodies are described in terms of their two functional domains. Antigen recognition is mediated by the Fab (antigen binding fragment) region of the antibody, while effector functions are mediated by the Fc (crystallizable fragment) region. The binding of antibody to antigen triggers destruction of the antigen by phagocytic white blood cells such as macrophages and neutrophils. These cells express surface Fc receptors that specifically bind to the Fc region of the antibody and allow the phagocytic cells to destroy antibody-bound antigen. Fc receptors are single-pass transmembrane glycoproteins containing about 350 amino acids whose extracellular portion typically contains two or three Ig domains (Sears et al. (1990) J Immunol 144:371–378).

Preparation and Screening of Antibodies

Various hosts including mice, rats, rabbits, goats, llamas, camels, and human cell lines may be immunized by injection with an antigenic determinant. Adjuvants such as Freund's, mineral gels, and surface active substances such as lysolecithin, pluronic polyols, polyanions, peptides, oil emulsions, keyhole limpet hemacyanin (KLH; Sigma-Aldrich), and dinitrophenol may be used to increase immunological response. In humans, BCG (bacilli Calmette-Guerin) and *Corynebacterium parvum* increase response. The antigenic determinant may be an oligopeptide, peptide, or protein. When the amount of antigenic determinant allows immunization to be repeated, specific polyclonal antibody with high affinity can be obtained (Klinman and Press (1975) Transplant Rev 24:41–83). Oligopeptides which may contain between about five and about fifteen amino acids identical to a portion of the endogenous protein may be fused with proteins such as KLH in order to produce antibodies to the chimeric molecule.

Monoclonal antibodies may be prepared using any technique which provides for the production of antibodies by continuous cell lines in culture. These include the hybridoma technique, the human B-cell hybridoma technique, and the EBV-hybridoma technique (Kohler et al. (1975) Nature 256:495–497; Kozbor et al. (1985) J Immunol Methods 81:31–42; Cote et al. (1983) Proc Natl Acad Sci 80:2026–2030; and Cole et al. (1984) Mol Cell Biol 62:109–120).

Chimeric antibodies may be produced by techniques such as splicing of mouse antibody genes to human antibody genes to obtain a molecule with appropriate antigen specificity and biological activity (Morrison et al. (1984) Proc Natl Acad Sci 81:6851–6855; Neuberger et al. (1984) Nature 312:604–608; and Takeda et al. (1985) Nature 314:452–454). Alternatively, techniques described for antibody production may be adapted, using methods known in the art, to produce specific, single chain antibodies. Antibodies with related specificity, but of distinct idiotypic composition, may be generated by chain shuffling from random combinatorial immunoglobulin libraries (Burton (1991) Proc Natl Acad Sci 88:10134–10137). Antibody fragments which contain specific binding sites for an antigenic determinant may also be produced. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 246:1275–1281).

Antibodies may also be produced by inducing production in the lymphocyte population or by screening immunoglobulin libraries or panels of highly specific binding reagents as disclosed in Orlandi et al. (1989; Proc Natl Acad Sci 86:3833–3837) or Winter et al. (1991; Nature 349:293–299). A protein may be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art.

Antibody Specificity

Various methods such as Scatchard analysis combined with radioimmunoassay techniques may be used to assess the affinity of particular antibodies for a protein. Affinity is expressed as an association constant, $K_a$, which is defined as the molar concentration of protein-antibody complex divided by the molar concentrations of free antigen and free antibody under equilibrium conditions. The $K_a$ determined for a preparation of polyclonal antibodies, which are heterogeneous in their affinities for multiple antigenic determinants, represents the average affinity, or avidity, of the antibodies. The $K_a$ determined for a preparation of monoclonal antibodies, which are specific for a particular antigenic determinant, represents a true measure of affinity. High-affinity antibody preparations with $K_a$ ranging from about $10^9$ to $10^{12}$ L/mole are commonly used in immunoassays in which the protein-antibody complex must withstand rigorous manipulations. Low-affinity antibody preparations with $K_a$ ranging from about $10^6$ to $10^7$ L/mole are preferred for use in immunopurification and similar procedures which ultimately require dissociation of the protein, preferably in active form, from the antibody (Catty (1988) *Antibodies, Volume I: A Practical Approach*, IRL Press, Washington D.C.; Liddell and Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing about 5–10 mg specific antibody/ml, is generally employed in procedures requiring precipitation of protein-antibody complexes. Procedures for making antibodies, evaluating antibody specificity, titer, and avidity, and guidelines for antibody quality and usage in various applications, are discussed in Catty (supra) and Ausubel (supra) pp. 11.1–11.31.

Diagnostics

Differential expression of CTTP, as detected using CTTP, cDNA encoding CTTP, or an antibody that specifically binds CTTP, and at least one of the assays below can be used to diagnose a neoplastic disorder and in particular colon and lung cancers.

Labeling of Molecules for Assay

A wide variety of reporter molecules and conjugation techniques are known by those skilled in the art and may be used in various nucleic acid, amino acid, and antibody assays. Synthesis of labeled molecules may be achieved using kits such as those supplied by Promega (Madison Wis.) or APB for incorporation of a labeled nucleotide such as $^{32}$P-dCTP (APB), Cy3-dCTP or Cy5-dCTP (Qiagen-Operon, Alameda Calif.), or amino acid such as $^{35}$S-menthione (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes).

Nucleic Acid Assays

The cDNAs, fragments, oligonucleotides, complementary RNAs, and peptide nucleic acids (PNA) may be used to detect and quantify differential gene expression for diagnosis of a disorder. Similarly antibodies which specifically bind CTTP may be used to quantitate the protein. Neoplastic disorders associated with such differential expression particularly include colon and lung cancers. The diagnostic assay may use hybridization or amplification technology to compare gene expression in a biological sample from a patient to standard samples in order to detect differential gene expression. Qualitative or quantitative methods for this comparison are well known in the art.

Expression Profiles

A gene expression profile comprises the expression of a plurality of cDNAs as measured by after hybridization with a sample. The cDNAs of the invention may be used as elements on a array to produce a gene expression profile. In one embodiment, the array is used to diagnose or monitor the progression of disease. Researchers can assess and catalog the differences in gene expression between healthy and diseased tissues or cells.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose or stage that disorder.

By analyzing changes in patterns of gene expression, disease can be diagnosed at earlier stages before the patient is symptomatic. The invention can be used to formulate a prognosis and to design a treatment regimen. The invention can also be used to monitor the efficacy of treatment. For treatments with known side effects, the array is employed to improve the treatment regimen. A dosage is established that causes a change in genetic expression patterns indicative of successful treatment. Expression patterns associated with the onset of undesirable side effects are avoided. This approach may be more sensitive and rapid than waiting for the patient to show inadequate improvement, or to manifest side effects, before altering the course of treatment.

In another embodiment, animal models which mimic a human disease can be used to characterize expression profiles associated with a particular condition, disease, or disorder; or treatment of the condition, disease, or disorder. Novel treatment regimens may be tested in these animal models using arrays to establish and then follow expression profiles over time. In addition, arrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

Protein Assays

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and protein and antibody arrays. Such immunoassays typically involve the measurement of complex formation between the protein and its specific antibody. These assays and their quantitation against purifed, labeled standards are well known in the art (Ausubel, supra, unit 10.1–10.6). A two-site, monoclonal-based immunoassay utilizing antibodies reactive to two non-interfering epitopes is preferred, but a competitive binding assay may be employed (Pound (1998) *Immunochemical Protocols*, Humana Press, Totowa N.J.).

These methods are also useful for diagnosing diseases that show differential protein expression. Normal or standard values for protein expression are established by combining body fluids or cell extracts taken from a normal mammalian or human subject with specific antibodies to a protein under conditions for complex formation. Standard values for complex formation in normal and diseased tissues are established by various methods, often photometric means. Then complex formation as it is expressed in a subject sample is compared with the standard values. Deviation from the normal standard and toward the diseased standard provides parameters for disease diagnosis or prognosis while deviation away from the diseased and toward the normal standard may be used to evaluate treatment efficacy.

Recently, antibody arrays have allowed the development of techniques for high-throughput screening of recombinant antibodies. Such methods use robots to pick and grid bacteria containing antibody genes, and a filter-based ELISA to screen and identify clones that express antibody fragments. Because liquid handling is eliminated and the clones are arrayed from master stocks, the same antibodies can be spotted multiple times and screened against multiple antigens simultaneously. Antibody arrays are highly useful in the identification of differentially expressed proteins. (See de Wildt et al. (2000) Nature Biotechnol 18:989–94.)

Therapeutics

Expression profiles clearly show the role and differential increase in expression of CTTP in neoplastic disorders and in particular, in colon and lung cancers.

In one embodiment,. when decreased expression or activity of the protein is desired, an antibody, antagonist, inhibitor, a pharmaceutical agent or a composition containing one or more of these molecules may be delivered to a subject in need of such treatment. Such delivery may be effected by methods well known in the art and may include delivery by an antibody that specifically binds the protein. For therapeutic use, monoclonal antibodies are used to block an active site, inhibit dimer formation, trigger apoptosis and the like.

In another embodiment, when increased expression or activity of the protein is desired, the protein, an agonist, an enhancer, a pharmaceutical agent or a composition containing one or more of these molecules may be delivered to a subject in need of such treatment. Such delivery may be effected by methods well known in the art and may include delivery of a pharmaceutical agent by an antibody specifically targeted to the protein.

Any of the cDNAs, complementary molecules, or fragments thereof, proteins or portions thereof, vectors delivering these nucleic acid molecules or expressing the proteins, therapeutic antibodies, and ligands binding the cDNA or protein may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the gene encoding CTTP. Oligonucleotides designed to inhibit transcription initiation are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, or the modification of adenine, cytidine, guanine, thymine, and uridine with acetyl-, methyl-, thio- groups renders the molecule more resistant to endogenous endonucleases.

cDNA Therapeutics

The cDNAs of the invention can be used in gene therapy. cDNAs can be delivered ex vivo to target cells, such as cells of bone marrow. Once stable integration and transcription and or translation are confirmed, the bone marrow may be reintroduced into the subject. Expression of the protein encoded by the cDNA may correct a disorder associated with mutation of a normal sequence, reduction or loss of an endogenous target protein, or overepression of an endogenous or mutant protein. Alternatively, cDNAs may be delivered in vivo using vectors such as retrovirus, adenovirus, adeno-associated virus, herpes simplex virus, and bacterial plasmids. Non-viral methods of gene delivery include cationic liposomes, polylysine conjugates, artificial viral envelopes, and direct injection of DNA (Anderson (1998) Nature 392:25–30; Dachs et al. (1997) Oncol Res 9:313–325; Chu et al. (1998) J Mol Med 76(3–4):184–192; Weiss et al. (1999) Cell Mol Life Sci 55(3):334–358; Agrawal (1996) *Antisense Therapeutics*, Humana Press, Totowa N.J.; and August et al. (1997) *Gene Therapy* (Advances in Pharmacology, Vol. 40), Academic Press, San Diego Calif.).

Monoclonal Antibody Therapeutics

Antibodies, and in particular monoclonal antibodies, that specifically bind a particular protein, enzyme, or receptor and block its overexpression are now being used therapeutically. The first widely accepted therapeutic antibodies were HERCEPTIN (Trastuzumab, Genentech, S. San Francisco Calif.) and GLEEVEC (imatinib mesylate, Norvartis Pharmaceuticals, East Hanover N.J.). HERCEPTIN is a humanized antibody approved for the treatment of HER2 positive metastatic breast cancer. It is designed to bind and block the function of overexpressed HER2 protein. GLEEVEC is indicated for the treatment of patients with Philadelphia chromosome positive (Ph+) chronic myeloid leukemia (CML) in blast crisis, accelerated phase, or in chronic phase after failure of interferon-alpha therapy. A second indication for GLEEVEC is treatment of patients with KIT (CD117) positive unresectable and/or metastatic malignant gastrointestinal stromal tumors. Other monoclonal antibodies are in various stages of clinical trials for indications such as prostate cancer, lymphoma, melanoma, pneumococcal infections, rheumatoid arthritis, psoriasis, systemic lupus erythematosus, and the like.

Screening and Purification Assays

The cDNA encoding CTTP may be used to screen a library or a plurality of molecules or compounds for specific binding affinity. The libraries may be antisense molecules, artificial chromosome constructions, branched nucleic acid molecules, DNA molecules, peptides, peptide nucleic acid, proteins such as transcription factors, enhancers, or repressors, RNA molecules, ribozymes, and other ligands which regulate the activity, replication, transcription, or translation of the endogenous gene. The assay involves combining a polynucleotide with a library or plurality of molecules or compounds under conditions allowing specific binding, and detecting specific binding to identify at least one molecule which specifically binds the cDNA.

In one embodiment, the cDNA of the invention may be incubated with a plurality of purified molecules or compounds and binding activity determined by methods well known in the art, e.g., a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a protein to purify a ligand would involve combining the protein with a sample under conditions to allow specific binding, detecting specific binding between the protein and ligand, recovering the bound protein, and using a chaotropic agent to separate the protein from the purified ligand.

In a preferred embodiment, CTTP may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands, and the specificity of binding or formation of complexes between the expressed protein and the ligand can be measured. Depending on the particular kind of molecules or compounds being screened, the assay may be used to identify agonists, antagonists, antibodies, DNA molecules, small drug molecules, immunoglobulins, inhibitors, mimetics, peptides, peptide nucleic acids, proteins, and RNA molecules or any other ligand, which specifically binds the protein.

In one aspect, this invention contemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein. Molecules or compounds identified by screening may be used in a mammalian model system to evaluate their toxicity or therapeutic potential.

Pharmaceutical Compositions

Pharmaceutical compositions may be formulated and administered, to a subject in need of such treatment, to attain a therapeutic effect. Such compositions contain the instant protein, agonists, antibodies specifically binding the protein, antagonists, inhibitors, or mimetics of the protein. Compositions may be manufactured by conventional means such as mixing, dissolving, granulating, dragee-making, levigating, emulsifying, encapsulating, entrapping, or lyophilizing. The composition may be provided as a salt, formed with acids such as hydrochloric, sulfuric, acetic, lactic, tartaric, malic, and succinic, or as a lyophilized powder which may be combined with a sterile buffer such as saline, dextrose, or water. These compositions may include auxiliaries or excipients which facilitate processing of the active compounds.

Auxiliaries and excipients may include coatings, fillers or binders including sugars such as lactose, sucrose, mannitol, glycerol, or sorbitol; starches from corn, wheat, rice, or potato; proteins such as albumin, gelatin and collagen; cellulose in the form of hydroxypropylmethyl-cellulose, methyl cellulose, or sodium carboxymethylcellulose; gums including arabic and tragacanth; lubricants such as magnesium stearate or talc; disintegrating or solubilizing agents such as the, agar, alginic acid, sodium alginate or cross-linked polyvinyl pyrrolidone; stabilizers such as carbopol gel, polyethylene glycol, or titanium dioxide; and dyestuffs or pigments added for identify the product or to characterize the quantity of active compound or dosage.

These compositions may be administered by any number of routes including oral, intravenous, intramuscular, intra-arterial, intramedullary, intrathecal, intraventricular, transdermal, subcutaneous, intraperitoneal, intranasal, enteral, topical, sublingual, or rectal.

The route of administration and dosage will determine formulation; for example, oral administration may be accomplished using tablets, pills, dragees, capsules, liquids, gels, syrups, slurries, or suspensions; parenteral administration may be formulated in aqueous, physiologically compatible buffers such as Hanks' solution, Ringer's solution, or physiologically buffered saline. Suspensions for injection may be aqueous, containing viscous additives such as sodium carboxymethyl cellulose or dextran to increase the viscosity, or oily, containing lipophilic solvents such as sesame oil or synthetic fatty acid esters such as ethyl oleate or triglycerides, or liposomes. Penetrants well known in the art are used for topical or nasal administration.

Toxicity and Therapeutic Efficacy

A therapeutically effective dose refers to the amount of active ingredient which ameliorates symptoms or condition. For any compound, a therapeutically effective dose can be estimated from cell culture assays using normal and neoplastic cells or in animal models. Therapeutic efficacy, toxicity, concentration range, and route of administration may be determined by standard pharmaceutical procedures using experimental animals.

The therapeutic index is the dose ratio between therapeutic and toxic effects—LD50 (the dose lethal to 50% of the population)/ED50 (the dose therapeutically effective in 50% of the population)—and large therapeutic indices are preferred. Dosage is within a range of circulating concentrations, includes an ED50 with little or no toxicity, and varies depending upon the composition, method of delivery, sensitivity of the patient, and route of administration. Exact dosage will be determined by the practitioner in light of factors related to the subject in need of the treatment.

Dosage and administration are adjusted to provide active moiety that maintains therapeutic effect. Factors for adjustment include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular composition.

Normal dosage amounts may vary from 0.1µg, up to a total dose of about 1 g, depending upon the route of administration. The dosage of a particular composition may be lower when administered to a patient in combination with other agents, drugs, or hormones. Guidance as to particular dosages and methods of delivery is provided in the pharmaceutical literature. Further details on techniques for formulation and administration may be found in the latest edition of *Remington's Pharmaceutical Sciences* (Mack Publishing, Easton Pa.).

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, gestation period, numbers of progeny, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to test whether long term administration may elicit toxicity, teratogenesis, or carcinogenesis. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the ability to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gene, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with pharmaceutical agents to obtain information on treatment of the analogous human condition. These methods have been used to model several human diseases.

Non-human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the protein may be used in any molecular biology techniques that have yet to be developed, provided the new techniques rely on properties of cDNAs that are currently known, including, but not limited to, such properties as the triplet genetic code and specific base pair interactions.

EXAMPLES

I cDNA Library Construction

The OVARDIT01 cDNA library was constructed using RNA isolated from diseased ovary tissue removed from a 39-year-old Caucasian female during total abdominal hysterectomy, bilateral salpingo-oophorectomy, dilation and curettage, partial colectomy, incidental appendectomy, and temporary colostomy. Pathology indicated the right and left adnexa were extensively involved by endometriosis. Endometriosis also involved the anterior and posterior serosal surfaces of the uterus and the cul-de-sac, mesentery, and muscularis propria of the sigmoid colon. Pathology for the associated tumor tissue indicated multiple (3 intramural, 1 subserosal) leiomyomata. Family history included hyperlipidemia, benign hypertension, atherosclerotic coronary artery disease, depressive disorder, brain cancer, and type II diabetes.

The frozen tissue was homogenized and lysed using a POLYTRON homogenizer (Brinkmann Instruments, Westbury N.J.) in guanidinium isothiocyanate solution. The lysates were centrifuged over a 5.7 M CsCl cushion using a SW28 rotor in an L8-70M Ultracentrifuge (Beckman Coulter, Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNAse at 37C. RNA extraction and precipitation were repeated as before. The mRNA was isolated with the OLIGOTEX kit (Qiagen, Chatsworth Calif.) and used to construct the cDNA library.

The mRNA was handled according to the recommended protocols in the SUPERSCRIPT plasmid system (Invitrogen). The cDNAs were fractionated on a SEPHAROSE CL4B column (APB), and those cDNAs exceeding 400 bp were ligated into pINCY plasmid. The plasmid was subsequently transformed into DH5α a competent cells (Invitrogen)

II Preparation and Sequencing of cDNAs

The cDNAs were prepared using a MICROLAB 2200 (Hamilton, Reno NV) in combination with DNA ENGINE thermal cyclers (MJ Research) and sequenced by the method of Sanger and Coulson (1975; J Mol Biol 94:441–48) using PRISM 377 or 373 DNA sequencing systems (ABI). Reading frame was determined using standard techniques.

The nucleotide sequences and/or amino acid sequences of the Sequence Listing were used to query sequences in the GenBank, SwissProt, BLOCKS, and Pima II databases. BLAST produced alignments of both nucleotide and amino acid sequences to determine sequence similarity. Because of the local nature of the alignments, BLAST was used in determining exact matches or in identifying homologs which may be of prokaryotic (bacterial) or eukaryotic (animal, fungal, or plant) origin. Other algorithms such as those of Smith et al. (1992; Protein Engineering 5:35–51) could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

III Extension of cDNAs

The cDNAs were extended using the cDNA clone and oligonucleotide primers. One primer was synthesized to initiate 5' extension of the known fragment, and the other, to initiate 3' extension of the known fragment. The initial primers were designed using primer analysis software to be about 22 to 30 nucleotides in length, to have a GC content of about 50% or more, and to anneal to the target sequence at temperatures of about 68C. to about 72C. Any stretch of nucleotides that would result in hairpin structures and primer-primer dimerizations was avoided.

Selected cDNA libraries were used as templates to extend the sequence. If extension was performed than one time, additional or nested sets of primers were designed. Preferred libraries have been size-selected to include larger cDNAs and random primed to contain more sequences with 5' or upstream regions of genes. Genomic libraries can be used to obtain regulatory elements extending into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Invitrogen), and Pfu DNA polymerase (Stratagene), with the following parameters for primer pair PCI A and PCI B (Incyte Genomics): The parameters for the cycles are 1: 94C, three min; 2: 94C, 15 sec; 3: 60C, one min; 4: 68C, two min; 5: 2, 3, and 4 repeated 20 times; 6: 68C, five min; and 7: storage at 4C. In the alternative, the parameters for primer pair T7 and SK+ (Stratagene) were as follows:1: 94C, three min; 2: 94C, 15 sec; 3: 57C, one min; 4: 68C, two min; 5: 2, 3, and 4 repeated 20 times; 6: 68C, five min; and 7: storage at 4C.

The concentration of DNA in each well was determined by dispensing 100 μl PICOGREEN quantitation reagent (0.25% reagent in 1× TE, v/v; Molecular Probes) and 0.5 μl of undiluted PCR product into each well of an opaque fluorimeter plate (Corning Life Sciences, Acton Mass.) and allowing the DNA to bind to the reagent. The plate was scanned in a Fluoroskan II (Labsystems Oy, Helsinki Finland) to measure the fluorescence of the sample and to quantify the concentration of DNA. A 5 μl to 10 μl aliquot of the reaction mixture was analyzed by electrophoresis on a 1% agarose minigel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37C. in 384-well plates in LB/2× carbenicillin liquid media.

The cells were lysed, and DNA was amplified using primers, Taq DNA polymerase (APB) and Pfu DNA polymerase (Stratagene) with the following parameters:1: 94C, three min; 2: 94C, 15 sec; 3: 60C, one min; 4: 72C, two min; 5: 2, 3, and 4 repeated 29 times; 6: 72C, five min; and 7: storage at 4C. DNA was quantified using PICOGREEN quantitation reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the PRISM BIGDYE terminator cycle sequencing kit (ABI).

IV Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST2 to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin and Altschul (1993; Proc Natl Acad Sci 90:5873–5877), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the stringency for an exact match was set from a lower limit of about 40 (with 1–2% error due to uncalled bases) to a 100% match of about 70.

The BLAST software suite (NCBI, Bethesda Md.), includes various sequence analysis programs including "blastn" that is used to align nucleotide sequences and BLAST2 that is used for direct pairwise comparison of either nucleotide or amino acid sequences. BLAST programs are commonly used with gap and other parameters set to default settings, e.g.: Matrix: BLOSUM62; Reward for match:1; Penalty for mismatch: −2; Open Gap:5 and Extension Gap:2 penalties; Gap x drop-off:50; Expect:10; Word Size:11; and Filter: on. Identity is measured over the entire length of a sequence. Brenner et al. (1998; Proc Natl Acad Sci 95:6073–6078, incorporated herein by reference) analyzed BLAST for its ability to identify structural homologs by sequence identity and found 30% identity is a reliable threshold for sequence alignments of at least 150 residues and 40%, for alignments of at least 70 residues.

The cDNAs of this application were compared with assembled consensus sequences or templates found in the LIFESEQ GOLD database (Incyte Genomics). Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, poly A tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another, and those having local similarity of at least 82% were combined and reassembled. Bins having templates with less than 95% local identity were split. Templates were subjected to analysis by STITCHER/EXON MAPPER algorithms that determine the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homology match as having an E-value (or probability score) of $\leq 1\times 10^{-8}$. The templates were also subjected to frameshift FASTx against GENPEPT, and homology match was defined as having an E-value of $\leq 1\times 10^{-8}$. Template analysis and assembly was described in U.S. patent application Ser. No. 09/276,534, filed Mar. 25, 1999.

Following assembly, templates were subjected to BLAST, motif, and other functional analyses and categorized in protein hierarchies using methods described in U.S. patent application Ser. No. 08/812,290 and U.S. patent application 08/811,758, both filed Mar. 6, 1997; in U.S. patent application Ser. No. 08/947,845, filed Oct. 9, 1997; and in U.S. patent application Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.). The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

V Northern Analysis and Transcript Imaging

Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook, supra, ch. 7 and Ausubel, supra, ch. 4 and 16.)

Analogous computer techniques applying BLAST are used to search for identical or related molecules in nucleotide databases such as GenBank or the LIFESEQ database (Incyte Genomics). This analysis is faster than multiple membrane-based hybridizations. In addition, the sensitivity of the computer search can be modified to determine whether any particular match is categorized as exact or homologous. The basis of the search is the product score, which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding CTTP occurs. Abundance and percent abundance are also reported. Abundance directly reflects the number of times a particular transcript is represented in a cDNA library, and percent abundance is abundance divided by the total number of sequences examined in the cDNA library.

Transcript Imaging

A transcript image is performed using the LIFESEQ GOLD database (Incyte Genomics). This process allows assessment of the relative abundance of the expressed polynucleotides in all of the cDNA libraries and was described in U.S. Pat. No. 5,840,484, incorporated herein by reference. All sequences and cDNA libraries in the LIFESEQ database are categorized by system, organ/tissue and cell type. The categories include cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. Criteria for transcript imaging are selected from category, number of cDNAs per library, library description, disease indication, clinical relevance of sample, and the like.

For each category, the number of libraries in which the sequence was expressed are counted and shown over the total number of libraries in that category. For each library, the number of cDNAs are counted and shown over the total number of cDNAs in that library. In some transcript images, all enriched, normalized or subtracted libraries, which have high copy number sequences can be removed prior to processing, and all mixed or pooled tissues, which are considered non-specific in that they contain more than one tissue type or more than one subject's tissue, can be excluded from the analysis. Treated and untreated cell lines and/or fetal tissue data can also be excluded where clinical relevance is emphasized. Conversely, fetal tissue can be emphasized wherever elucidation of inherited disorders or differentiation of particular adult or embryonic stem cells into tissues or organs (such as heart, kidney, nerves or pancreas) would be aided by removing clinical samples from the analysis. Transcript imaging can also be used to support data from other methodologies such as hybridization, guilt-by-association and array technologies.

VI Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNA encoding CTTP that have been mapped result in the assignment of all related regulatory and coding sequences to the same location. The genetic map locations are described as ranges, or intervals, of human chromosomes. The map position of an interval, in cm (which is roughly equivalent to 1 megabase of human DNA), is measured relative to the terminus of the chromosomal p-arm.

VII Hybridization and Amplication Technologies and Analyses

Tissue Sample Preparation

Normal and cancerous tissue samples are described by donor identification number in the table below. The first column shows the donor ID; the second, donor age/sex; the third column, a description of the colon cancer' the fourth column, classification of the tumor; and the fifth column, the source.

| Donor | Age/Sex * | Tissue and Description | Stage | Source |
|---|---|---|---|---|
| 3579 | 55/M | colon; well differentiated adenocarcinoma | Dukes' C; TMN T2N1 | HCI |
| 3580 | 38/M | colon; poorly differentiated, metastatic adenoCA | T3N1MX | HCI |
| 3581 | U/M | rectal; tumor | NA | HCI |
| 3582 | 78/M | colon; moderately differentiated adenocarcinoma | TMN T4N2MX | HCI |
| 3583 | 58/M | colon; tubulovillous adenoma (hyperplastic polyp) | NA | HCI |
| 3647 | 83/U | colon; invasive moderately differentiated adenocarcinoma (tubular adenoma) | TMN T3N1MX | HCI |
| 3649 | 86/U | colon; invasive well-differentiated adenoCA | NA | HCI |
| 3479 | 68/M | colon; adenocarcinoma | NA | HCI |
| 4614 | 67/U | colon; moderately differentiated adenocarcinoma | Dukes' B; TMN T3N0 | HCI |
| 7164 | 79/M | lung; pulmonary carcinoid | stage IA | RCIC |
| 7186 | 61/M | lung; atypical carcinoid | stage IA | RCIC |
| 7192 | 54/F | lung; large cell carcinoma | stage IB | RCIC |
| 7976 | U/U | lung; non-small cell lung cancer | | Clinomics |
| 8306 | 73/M | colorectal; metastatic adenocarcinoma | Dukes' | Asterand |
| 8310 | U/U | lung, normal pool | C; T3N1M0 | RCIC |
| 8403 | 54/F | colon; well differentiated adenocarcinoma | Dukes' C | Asterand |

-continued

| Donor | Age/Sex * | Tissue and Description | Stage | Source |
|---|---|---|---|---|
| 9007 | U/U | lung, normal pool | | RCIC |
| 9573 | 60/F | colon; moderately differentiated adenocarcinoma | Dukes C; T2N2M0 | Asterand |
| 9574 | 34/F | colon; well differentiated metastatic adenoCA | Dukes C; T2N1M0 | Asterand |
| 9575 | 60/M | colon; moderately differentiated metastatic adenoCA | Dukes C; TXN1-2M0 | Asterand |
| 9576 | 65/M | colon; well differentiated adenocarcinoma | Dukes C; T3N2M0 | Asterand |
| 9577 | 46/F | colon; well differentiated adenocarcinoma | Dukes C; TXN1-2M0 | Asterand |
| 9697 | 39/M | colon; metastatic mucinous adenocarcinoma | Unknown | CHTN |

*Abbreviations: CA = carcinoma, U = unknown, NA = not available

In FIG. 3, the normalized, first-strand synthesis, cDNA preparations of normal, human heart, brain (whole), lung, liver, skeletal muscle, kidney, pancreas, spleen, thymus, prostate, ovary, small intestine, peripheral blood leukocyte, and colon tissues were obtained from Clontech. Additional cDNA preparations of human, adult, normal thyroid, pituitary, and adrenal tissues were obtained from Clinomics Bioscience (Pittsfield Mass.).

The colorectal adenocarcinoma cell lines shown in FIG. 5 were obtained from ATCC and cultured according to the suppliers specifications. The cell lines were LS123, LS174T, HCT116, CaCo2, HT29, SW480, SW620 and Colo205.

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37C. for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning Life Sciences) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110C. oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Ma.) for 30 min at 60C.; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100C. for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37C. for 10 min. The labeling reaction is stopped by adding 5 µl of 0.2M EDTA, and probe is purified from unincorporated nucleotides using a PROBEQUANT G-50 microcolumn (APB). The purified probe is heated to 100C. for five min, snap cooled for two min on ice, and used in membrane-based hybridizations as described below.

Probe Preparation for QPCR

Probes for the QPCR were prepared according to the ABI protocol.

Probe Preparation for Polymer Coated Slide Hybridization

The following method was used for the preparation of probes for the microarray analysis presented in FIG. 3. Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 µl TE buffer and adding 5 µl 5× buffer, 1 µl 0.1 M DTT, 3 µl Cy3 or Cy5 labeling mix, 1 µl RNAse inhibitor, 1 µl reverse transcriptase, and 5 µl 1× yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37C. for two hr. The reaction mixture is then incubated for 20 min at 85C., and probes are purified using two successive CHROMA SPIN+TE 30 columns (Clontech, Palo Alto Calif.). Purified probe is ethanol precipitated by diluting probe to 90 µl in DEPC-treated water, adding 2 µl 1 mg/ml glycogen, 60 µl 5 M sodium acetate, and 300 µl 100% ethanol. The probe is centrifuged for 20 min at 20,800×g, and the pellet is resuspended in 12 µl resuspension buffer, heated to 65C. for five min, and mixed thoroughly. The probe is heated and mixed as before and then stored on ice. Probe is used in high density array-based hybridizations as described below.

In situ Hybridization

In situ hybridization was used to determine the expression of CTTP in sectioned tissue. Fresh cryosections, ten microns thick, were removed from the freezer, immediately immersed in 4% paraformaldehyde for 10 minutes, rinsed in PBS, and acetylated in 0.1M TEA, pH 8.0, containing 0.25% (v/v) acetic anhydride. After the tissue equilibrated in 5× SSC, it was prehybridized in hybridization buffer (50% formamide, 5× SSC, 1× Denhardt's solution, 10% dextran sulfate, 1mg/ml herring sperm DNA).

Digoxygenin-labeled CTTP-specific RNA probes, sense and antisense nucleotides from about C479 to about nucleotide C847 of SEQ ID NO:2, were produced using PCR. Approximately 500 ng/ml of probe was used in overnight hybridizations at 65C. in hybridization buffer. Following hybridization, the sections were rinsed for 30 min in 2× SSC at room temperature, 1 hr in 2× SSC at 65C., and 1 hr in 0.1× SSC at 65C. The sections were equilibrated in PBS, blocked for 30 min in 10% DIG kit blocker (Roche Molecular Biochemicals, Indianapolis Ind.) in PBS, then incubated overnight at 4C. in 1:500 anti-DIG-AP. The following day, the sections were rinsed in PBS, equilibrated in detection buffer (0.1M Tris, 0.1M NaCl, 50 mM MgCl2, pH 9.5), and then incubated in detection buffer containing 0.175 mg/ml NBT and 0.35 mg/ml BCIP. The reaction was terminated in TE, pH 8. Tissue sections were counterstained with 1 microgram/ml DAPI and mounted in VECTASHIELD (Vector Laboratory, Burlingame Calif.).

Membrane-based Hybridization

Membranes are pre-hybridized in hybridization solution containing 1% Sarkosyl and 1× high phosphate buffer (0.5 M NaCl, 0.1 M Na$_2$HPO$_4$, 5 mM EDTA, pH 7) at 55C. for two hr. The probe, diluted in 15 ml fresh hybridization solution, is then added to the membrane. The membrane is hybridized with the probe at 55C. for 16 hr. Following hybridization, the membrane is washed for 15 min at 25C. in 1 mM Tris (pH 8.0), 1% Sarkosyl, and four times for 15 min each at 25C. in 1 mM Tris (pH 8.0). To detect hybridization complexes, XOMAT-AR film (Eastman Kodak, Rochester N.Y.) is exposed to the membrane overnight at −70C., developed, and examined visually.

Polymer Coated Slide-Based Hybridization The following method was used in the microarray analysis presented in Table 3. Probe is heated to 65C. for five min, centrifuged five min at 9400 rpm in a 5415C microcentrifuge (Eppendorf Scientific, Westbury N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 µl of 5× SSC in a corner of the chamber. The chamber containing the arrays is incubated for about 6.5 hr at 60C. The arrays are washed for 10 min at 45C. in 1× SSC, 0.1% SDS, and three times for 10 min each at 45C. in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20× microscope objective (Nikon, Melville N.Y.). The slide containing the array is placed on a computer-controled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Filters positioned between the array and the photomultiplier tubes are used to separate the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Ma.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

QPCR Analysis

For QPCR, cDNA was synthesized from 1 ug total RNA in a 25 ul reaction with 100 units M-MLV reverse transcriptase (Ambion, Austin TX), 0.5 mM dNTPs (Epicentre, Madison Wis.), and 40 ng/ml random hexamers (Fisher Scientific, Chicago IL). Reactions were incubated at 25C. for 10 minutes, 42C. for 50 minutes, and 70C. for 15 minutes, diluted to 500 ul, and stored at −30C. Alternatively, normal tissues were purchased from Clontech (Palo Alto Calif.) and Clinomics. PCR primers and probes (5' 6-FAM-labeled, 3' TAMRA) were designed using PRIMER EXPRESS 1.5 software (ABI) and synthesized by Biosearch Technologies (Novato Calif.) or ABI.

QPCR reactions were performed using an PRISM 7700 detection system (ABI) in 25 ul total volume with 5 ul cDNA template, 1× TAQMAN UNIVERSAL PCR master mix (ABI), 100 nM each PCR primer, 200 nM probe, and 1× VIC-labeled beta-2-microglobulin endogenous control (ABI). Reactions were incubated at 50C. for 2 minutes, 95C. for 10 minutes, followed by 40 cycles of incubation at 95C. for 15 seconds and 60C. for 1 minute. Emissions were measured once every cycle, and results were analyzed using SEQUENCE DETECTOR 1.7 software (ABI) and fold differences, relative concentration of mRNA as compared to standards, were calculated using the comparative $C_T$ method (ABI User Bulletin #2). QPCR was used to produce the data for FIGS. 3, 4, and 5

VIII Complementary Molecules

Antisense molecules complementary to the cDNA, from about 5 bp to about 5000 bp in length, are used to detect or inhibit gene expression. Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in triple helix base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if elements for inducing vector replication are used in the transformation/expression system.

Stable transformation of dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the protein.

IX Cell Transfections and Fractionations

Cell Transfections 293 cells (ATCC) were transiently transfected with an expression vector containing the cDNA encoding CTTP. The expression vector, pTRIEX-3 NEO (Novagen, Madison Wis.), contained the entire coding sequence and a C-terminal FLAG-tag. Transfections were performed using the FUGENE 6 transfection reagent (Roche Applied Science, Indianapolis Ind.) according to the manufacturer's specifications. Forty-eight hours after transfection, cells were harvested for subcellular fractionation or prepared as total cellular lysates for western analysis.

Subcellular Fractionation

Transfected 293 cells, HT29 cells and SW620 cells expressing CTTP were grown to confluence in 10 cm tissue culture dishes. Cell media was aspirated from the plate, and cells were rinsed with 10 mL PBS. Cells were scraped off the dish using 5 mL PBS and a rubber policeman and collected in a 15 mL Falcon tube (VWR, West Chester Pa.). The dish was rinsed with 5 ML PBS which was combined with the cells. The cells were centrifuged at 1,000× g for 5 minutes at 4C. The PBS was removed from the cell pellet, and 0.8 mL of hypotonic lysis buffer (10 mM Tris, pH 7.4, 0.2 mM $MgCl_2$, containing COMPLETE MINI, EDTA-free protease inhibitors; Roche Applied Science) was used to resuspend the pellet. After the suspension was placed on ice for 15 minutes, it was homogenized with 30 up-and-down strokes using a tight-fitting (type A) Wheaton dounce homogenizer (VWR). 200 uL of 5× sucrose (1.25M) and 2 uL of 0.5M EDTA was added to the homogenate. The nuclei were separated by centrifugation at 1,000× g for 10 minutes at 4C., and the supernatant was removed from the pellet (P1) and transferred to a new tube. A second centrifugation at 10,000× g for 10 minutes separated the mitochondria (P10), and the supernatant was transferred to a new tube. This supernatant was centrifuged at 100,000× g for 45 minutes at 4C. to separate the plasma membrane fraction (P100) from the supernatant (S100). All pellets were resuspended in an equal volume of sucrose/Tris/EDTA buffer (0.25M sucrose, 10 mM Tris, pH 7.4, 1 mM EDTA).

Total Cellular Lysate Generation

Confluent 10 cm culture dishes of transiently transfected 293 cells, HT29 cells, or SW620 cells expressing CTTP were rinsed with 10 mL PBS. Cells were lysed in 1 mL of NP40/deoxycholate lysis buffer (50 mM Tris, pH 8.0, 150 mM NaCl, 1% NP-40, 0.5% sodium deoxycholate. COMPLETE MINI protease inhibitors (Roche Applied Science) were added fresh immediately before use. The cell lysate was scraped off the dish and clarified by centrifugation at 10,000× g for 10 minutes at 4C.

X Production of Specific Antibodies

The amino acid sequence of CTTP was analyzed using LASERGENE software (DNASTAR) to determine regions of high immunogenicity. SynPep synthesized the oligopeptide extending from residue D125 to residue A140 of SEQ ID NO:1 and conjugated the synthetic oligopeptide to KLH (Sigma-Aldrich).

Covance immunized rabbits with the oligopeptide-KLH complex in complete Freund's adjuvant, and the resulting antisera were tested for antipeptide activity by standard ELISA methods. The antisera was also tested for specific recognition of CTTP. Antisera that reacted positively with CTTP was affinity purified on a column containing beaded agarose resin to which the synthetic oligopeptide had been conjugated (Covance). The column was equilibrated using 12 mL IMMUNOPURE Gentle Binding buffer (Pierce Chemical, Rockford Ill.). Three mL of rabbit antisera was combined with one mL of binding buffer and added to the top of the column. The column was capped on the top and bottom, and antisera was allowed to bind with gentle shaking at room temperature for 30 min. The column was allowed to settle for 30 min, drained by gravity flow, and washed with 16 mL binding buffer (4×4 mL additions of buffer). The antibody was eluted in one ml fractions with IMMUNOPURE Gentle Elution buffer (Pierce), and absorbance at 280 nm was determined. Peak fractions were pooled and dialyzed against 50 mM Tris, pH 7.4, 100 mM NaCl, and 10% glycerol. After dialysis, the concentration of the purified antibody was determined using the BCA assay (Pierce), aliquoted, and frozen.

XI Immunopurification Using Antibodies

Naturally occurring or recombinantly produced protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the purified protein is collected.

XII Western Analysis

Electrophoresis and Blotting

Samples containing protein were mixed in 2× loading buffer, heated to 95 C. for 3–5 min, and loaded on 4–12% NUPAGE Bis-Tris precast gel (Invitrogen). Unless indicated, equal amounts of total protein were loaded into each well. The gel was electrophoresed in 1× MES or MOPS running buffer (Invitrogen) at 200 V for approximately 45 min on an Xcell II apparatus (Invitrogen) until the RAINBOW marker (APB) had resolved, and dye front approached the bottom of the gel. The gel and its supports were removed from the apparatus and soaked in 1× transfer buffer (Invitrogen) with 10% methanol for a few minutes; and the PVDF membrane was soaked in 100% methanol for a few seconds to activate it. The membrane, the gel, and supports were placed on the TRANSBLOT SD transfer apparatus (Biorad, Hercules CA) and a constant current of 350 mAmps was applied for 90 min.

Conjugation with Antibody and Visualization

After the proteins were transferred to the membrane, it was blocked in 5% (w/v) non-fat dry milk in 1× phosphate buffered saline (PBS) with 0.1% Tween 20 detergent (blocking buffer) on a rotary shaker for at least 1 hr at room temperature or at 4C. overnight. After blocking, the buffer was removed, and 10 ml of primary antibody in blocking buffer was added and incubated on the rotary shaker for 1 hr at room temperature or overnight at 4C. The membrane was washed 3× for 10 min each with PBS-Tween (PBST), and secondary anti-body, conjugated to horseradish peroxidase, was added at a 1:3000 dilution in 10 ml blocking buffer. The membrane and solution were shaken for 30 min at room temperature and then washed three times for 10 min each with PBST.

The wash solution was carefully removed, and the membrane was moistened with ECL+chemiluminescent detection system (APB) and incubated for approximately 5 min. The membrane, protein side down, was placed on BIOMAX M film (Eastman Kodak) and developed for approximately 30 seconds.

XIII Antibody Arrays

Protein:protein Interactions

In an alternative to yeast two hybrid system analysis of proteins, an antibody array can be used to study protein-protein interactions and phosphorylation. A variety of protein ligands are immobilized on a membrane using methods well known in the art. The array is incubated in the presence of cell lysate until protein:antibody complexes are formed. Proteins of interest are identified by exposing the membrane to an antibody specific to the protein of interest. In the alternative, a protein of interest is labeled with digoxigenin (DIG) and exposed to the membrane; then the membrane is exposed to anti-DIG antibody which reveals where the protein of interest forms a complex. The identity of the proteins with which the protein of interest interacts is determined by the position of the protein of interest on the membrane.

Proteomic Profiles

Antibody arrays can also be used for high-throughput screening of recombinant antibodies. Bacteria containing antibody genes are robotically-picked and gridded at high density (up to 18,342 different double-spotted clones) on a filter. Up to 15 antigens at a time are used to screen for clones to identify those that express binding antibody fragments. These antibody arrays can also be used to identify proteins which are differentially expressed in samples (de Wildt, supra)

XIV Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XV Two-hybrid Screen

A yeast two-hybrid system, MATCHMAKER LexA Two-Hybrid system (Clontech Laboratories), is used to screen for peptides that bind the protein of the invention. A cDNA encoding the protein is inserted into the multiple cloning site of a pLexA vector, ligated, and transformed into *E. coli*. cDNA, prepared from mRNA, is inserted into the multiple cloning site of a pB42AD vector, ligated, and transformed into *E. coli* to construct a cDNA library. The pLexA plasmid and pB42AD-cDNA library constructs are isolated from *E. coli* and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30C. until the colonies have grown up and are counted. The colonies are pooled in a minimal volume of 1× TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30C. A sample of the culture is plated on SD/-Trp/-Ura media and incubated at 30C. until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the protein, is isolated from the yeast cells and characterized.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. An isolated cDNA comprising a polynucleotide encoding a protein having the amino acid sequence of SEQ ID NO:1 or the full a complement of a polynucleotide encoding a protein having the amino acid sequence of SEQ ID NO:1.

2. An isolated cDNA comprising a polynucleotide having the nucleic acid sequence of SEQ ID NO:2 or the full complement of SEQ ID NO:2.

3. A fragment of the polynucleotide of claim 2 wherein the fragment comprises from nucleotide G1 to nucleotide T332, or from nucleotide C479 to nucleotide C847, or from nucleotide G500 to nucleotide G792, or from nucleotide G1083 to nucleotide G1226 of SEQ ID NO:2 or the full complements thereof.

4. A fragment of the polynucleotide of claim 2 wherein the fragment comprises from nucleotide C512 to nucleotide G575 of SEQ ID NO:2 or the full complement thereof.

5. A composition comprising the cDNA of claim 1 and a labeling moiety.

6. A vector comprising the cDNA of claim 1.

7. An isolated host cell comprising the vector of claim 6.

8. A method for producing a protein that is encoded by a cDNA, the method comprising:
   a) culturing the host cell of claim 7 under conditions for protein expression; and
   b) recovering the protein from the host cell culture
   wherein the cDNA comprises a polynucleotide encoding the protein having the amino acid sequence of SEQ ID NO:1.

9. A composition comprising the cDNA of claim 2 and a labeling moiety.

* * * * *

SEQUENCE LISTING

<160> NUMBER OF SEQ ID NOS: 9

<210> SEQ ID NO 1
<211> LENGTH: 320
<212> TYPE: PRT
<213> ORGANISM: Homo sapiens
<220> FEATURE:
<221> NAME/KEY: misc_feature
<223> OTHER INFORMATION: Incyte ID No: 4901066CD1

<400> SEQUENCE: 1

Met Thr Leu Trp Asn Gly Val Leu Pro Phe Tyr Pro Gln Pro Arg
 1               5                  10                  15

His Ala Ala Gly Phe Ser Val Pro Leu Leu Ile Val Ile Leu Val
                20                  25                  30

Phe Leu Ala Leu Ala Ala Ser Phe Leu Leu Ile Leu Pro Gly Ile
                35                  40                  45

Arg Gly His Ser Arg Trp Phe Trp Leu Val Arg Val Leu Leu Ser
                50                  55                  60

Leu Phe Ile Gly Ala Glu Ile Val Ala Val His Phe Ser Ala Glu
                65                  70                  75

-continued

```
Trp Phe Val Gly Thr Val Asn Thr Asn Thr Ser Tyr Lys Ala Phe
             80                  85                  90

Ser Ala Ala Arg Val Thr Ala Arg Val Gly Leu Leu Val Gly Leu
             95                 100                 105

Glu Gly Ile Asn Ile Thr Leu Thr Gly Thr Pro Val His Gln Leu
            110                 115                 120

Asn Glu Thr Ile Asp Tyr Asn Glu Gln Phe Thr Trp Arg Leu Lys
            125                 130                 135

Glu Asn Tyr Ala Ala Glu Tyr Ala Asn Ala Leu Glu Lys Gly Leu
            140                 145                 150

Pro Asp Pro Val Leu Tyr Leu Ala Glu Lys Phe Thr Pro Ser Ser
            155                 160                 165

Pro Cys Gly Leu Tyr His Gln Tyr His Leu Ala Gly His Tyr Ala
            170                 175                 180

Ser Ala Thr Leu Trp Val Ala Phe Cys Phe Trp Leu Leu Ser Asn
            185                 190                 195

Val Leu Leu Ser Thr Pro Ala Pro Leu Tyr Gly Leu Ala Leu
            200                 205                 210

Leu Thr Thr Gly Ala Phe Ala Leu Phe Gly Val Phe Ala Leu Ala
            215                 220                 225

Ser Ile Ser Ser Val Pro Leu Cys Pro Leu Arg Leu Gly Ser Ser
            230                 235                 240

Ala Leu Thr Thr Gln Tyr Gly Ala Ala Phe Trp Val Thr Leu Ala
            245                 250                 255

Thr Gly Val Leu Cys Leu Phe Leu Gly Gly Ala Val Val Ser Leu
            260                 265                 270

Gln Tyr Val Arg Pro Ser Ala Leu Arg Thr Leu Leu Asp Gln Ser
            275                 280                 285

Ala Lys Asp Cys Ser Gln Glu Arg Gly Gly Ser Pro Leu Ile Leu
            290                 295                 300

Gly Asp Pro Leu His Lys Gln Ala Ala Leu Pro Asp Leu Lys Cys
            305                 310                 315

Ile Thr Thr Asn Leu
            320

<210> SEQ ID NO 2
<211> LENGTH: 1421
<212> TYPE: DNA
<213> ORGANISM: Homo sapiens
<220> FEATURE:
<221> NAME/KEY: misc_feature
<223> OTHER INFORMATION: Incyte ID No: 4901066CB1

<400> SEQUENCE: 2
gaaccaggaa agtaacggct acagacagtg agaaatagtt tcgctcgccg gctagaaaaa      60
ctctgtcggt accaacccca gagcgttgag agcagcccac ctccacgctt ccttaacgga    120
gaggtgcagg actcagactt caccagccca ctcggtccca gccttgtacg caaagagacg    180
ccaaggacgc gctctcccgc gtccaggcag ccccagcttg ctggcttgcc tgcccgcctg    240
cgtgcagcac tcggccggcg tgcagcatga ccctgtggaa cggcgtactg ccttttttacc    300 cccagccccg gcatgccgca ggcttcagcg ttccactgct catcgttatt ctagtgtttt    360
tggctctagc agcaagcttc ctgctcatct tgccggggat ccgtggccac tcgcgctggt    420
tttggttggt gagagttctt ctcagtctgt tcataggcgc agaaattgtg gctgtgcact    480
tcagtgcaga atggttcgtg ggtacagtga acaccaacac atcctacaaa gccttcagcg    540
```

-continued

```
cagcgcgcgt tacagcccgt gtcggtctgc tcgtgggcct ggagggcatt aatattacac    600
tcacagggac cccagtgcat cagctgaacg agaccattga ctacaacgag cagttcacct    660
ggcgtctgaa agagaattac gccgcggagt acgcgaacgc actggagaag gggctgccgg    720
acccagtgct ctacctggcg gagaagttca caccgagtag cccttgcggc ctgtaccacc    780
agtaccacct ggcgggacac tacgcctcgg ccacgctatg ggtggcgttc tgcttctggc    840
tcctctccaa cgtgctgctc tccacgccgg ccccgctcta cggaggcctg gcactgctga    900
ccaccggagc cttcgcgctc ttcggggtct tcgccttggc ctccatctct agcgtgccgc    960
tctgcccgct ccgcctaggc cctccgcgc tcaccactca gtacggcgcc gccttctggg    1020
tcacgctggc aaccggcgtc ctgtgcctct tcctcggagg ggccgtggtg agtctccagt    1080
atgttcggcc cagcgctctt cgcacccttc tggaccaaag cgccaaggac tgcagccagg    1140
agagaggggg ctcacctctt atcctcggcg acccactgca caagcaggcc gctctcccag    1200
acttaaaatg tatcaccact aacctgtgag ggggacccaa tctggactcc ttccccgcct    1260
tgggacatcg caggccggga agcagtgccc gccaggcctg gccaggaga gctccaggaa    1320 gggcactgag cgctgctggc gcgaggcctc ggacatccgc aggcaccagg gaaagtctcc    1380
tggggcgatc tgtaaataaa cctttttttc ttttgttttt t                       1421
```

<210> SEQ ID NO 3
<211> LENGTH: 346
<212> TYPE: DNA
<213> ORGANISM: Homo sapiens
<220> FEATURE:
<221> NAME/KEY: misc_feature
<223> OTHER INFORMATION: Incyte ID No: 1752794F6
<220> FEATURE:
<221> NAME/KEY: unsure
<222> LOCATION: 91, 188, 206, 291, 337
<223> OTHER INFORMATION: a, t, c, g, or other

<400> SEQUENCE: 3

```
cttggcctcc atctctagcg tgccgctctg cccgctccgc ctaggctcct ccgcgctcac    60
cactcagtac ggcgccgcct tctgggtcac nctggcaacc ggcgtcctgt gcctcttcct    120
cggaggggcc gtggtgagtc tccagtatgt tcggcccagc gctcttcgca cccttctgga    180
ccaaagcncc aaggactgca gccagnagag aggggctca cctcttatcc tcggcgaccc    240
cactgcacaa gcaggccgct ctcccagact taaaatgtat caccactaac ntgtgagggg    300
gacccaatct ggatccttcc ccgcttggga atcgcantcc gggaag                    346
```

<210> SEQ ID NO 4
<211> LENGTH: 1420
<212> TYPE: DNA
<213> ORGANISM: Homo sapiens
<220> FEATURE:
<221> NAME/KEY: misc_feature
<223> OTHER INFORMATION: Incyte ID No: 3221661CA2

<400> SEQUENCE: 4

```
gaaccaggaa agtaacggct acagacagtg agaaatagtt tcgctcgccg gctagaaaaa    60
ctctgtcggt accaccccca gagcgttgag agcagcccac ctccacgctt ccttaacgga    120
gaggtgcagg actcagactt caccagccca ctcggtccca gccttgtacg caaagagacg    180
ccaaggacgc gctctcccgc gtccaggcag cccagcttg ctggcttgcc tgcccgcctg    240
cgtgcagcac tcggccggcg tgcagcatga ccctgtggaa cggcgtactg ccttttttacc    300
```

-continued

| | |
|---|---|
| cccagccccg gcatgccgca ggcttcagcg ttccactgct catcgttatt ctagtgtttt | 360 |
| tggctctagc agcaagcttc ctgctcatct tgccggggat ccgtgccac tcgcgctggt | 420 |
| tttggttggt gagagttctt ctcagtctgt tcataggcgc agaaattgtg gctgtgcact | 480 |
| tcagtgcaga atggttcgtg ggtacagtga acaccaacac atcctacaaa gccttcagcg | 540 |
| cagcgcgcgt tacagcccgt gtcggtctgc tcgtgggcct ggagggcatt aatattacac | 600 |
| tcacagggac cccagtgcat cagctgaacg agaccattga ctacaacgag cagttcacct | 660 |
| ggcgtctgaa agagaattac gccgcggagt acgcgaacgc actggagaag gggctgccgg | 720 |
| acccagtgct ctacctggcg gagaagttca caccgagtag cccttgcggc ctgtaccacc | 780 |
| agtaccacct ggcgggacac tacgcctcgg ccacgctatg ggtggcgttc tgcttctggc | 840 |
| tcctctccaa cgtgctgctc tccacgccgg ccccgctcta cggaggcctg gcactgctga | 900 |
| ccaccggagc cttcgcgctc ttcggggtct tcgccttggc ctccatctct agcgtgccgc | 960 |
| tctgcccgct ccgcctaggc tcctccgcgc tcaccactca gtacgcgcc gccttctggg | 1020 |
| tcacgctggc aaccggcgtc ctgtgcctct tcctcggagg ggccgtggtg agtctccagt | 1080 |
| atgttcggcc cagcgctctt cgcacccttc tggaccaaag cgccaaggac tgcagccagg | 1140 |
| agagagggg ctcacctctt atcctcggcg acccactgca caagcaggcc gctctcccag | 1200 |
| acttaaaatg tatcaccact aacctgtgag ggggacccaa tctggactcc ttccccgcct | 1260 |
| tgggacatcg caggccggga agcagtgccc gccaggcctg ggccaggaga gctccaggaa | 1320 |
| gggcactgag cgctgctggc gcgaggcctc ggacatccgc aggcaccagg gaaagtctcc | 1380 |
| tggggcgatc tgtaaataaa cctttttttc ttgggtttta | 1420 |

<210> SEQ ID NO 5
<211> LENGTH: 522
<212> TYPE: DNA
<213> ORGANISM: Homo sapiens
<220> FEATURE:
<221> NAME/KEY: misc_feature
<223> OTHER INFORMATION: Incyte ID No: 3221661R6
<220> FEATURE:
<221> NAME/KEY: unsure
<222> LOCATION: 455, 480, 483
<223> OTHER INFORMATION: a, t, c, g, or other

<400> SEQUENCE: 5

| | |
|---|---|
| gaaccaggaa agtaacggct acagacagtg agaaatagtt tcgctcgccg gctagaaaaa | 60 |
| ctctgtcggt accaacccca gagcgttgag agcagcccac ctccacgctt ccttaacgga | 120 |
| gaggtgcagg actcagactt caccagccca ctcggtccca gccttgtacg caaagagacg | 180 |
| ccaaggacgc gctctcccgc gtccaggcag ccccagcttg ctggcttgcc tgcccgcctg | 240 |
| cgtgcagcac tcggccggcg tgcagcatga ccctgtggaa cggcgtactg cctttttacc | 300 |
| cccagccccg gcatgccgca gtttcaagcg ttccactgct catcgttatt ctagtgtttt | 360 |
| tggtctagca gcaagttcct gtcatcttgc cggggatccg tggccactcg cgctggtttt | 420 |
| ggttggtgag agttcttctc agtctgttca taggngcaga aattgtggct gtgcacttcn | 480 |
| gtnagaatgg ttcgtgggta cattgacacc aaacacatcct ac | 522 |

<210> SEQ ID NO 6
<211> LENGTH: 506
<212> TYPE: DNA
<213> ORGANISM: Homo sapiens
<220> FEATURE:
<221> NAME/KEY: misc_feature
<223> OTHER INFORMATION: Incyte ID No: SBQA03652D1

```
<220> FEATURE:
<221> NAME/KEY: unsure
<222> LOCATION: 87, 89, 93, 95, 124, 178, 227, 253, 262, 279, 285, 287,
              293-294, 298, 300, 303, 312, 319-321, 323, 325, 327,
              332-333, 336, 343-344, 349, 377, 390, 405, 409-410, 412,
              415, 420, 423, 429, 432, 436-437, 444-445, 448, 452,
              454, 466, 469-471, 479, 483, 485, 492, 494, 499, 501,
              504
<223> OTHER INFORMATION: a, t, c, g, or other

<400> SEQUENCE: 6
actctagagg atcccctgt gcacttcagt cagaatggtt cgtgggtaca gtgaacacca    60
acacatccta caaagccttc agcgcancng gtntnacagc ccgtgtcggt ctgctcgtgg   120
gccnggaggg catgaatatt acactcacag ggaccccagt gcatcagctg agcgaganca   180
ttgactacaa cgagcagttc acctggcgtc tgaaagagaa ttacgcngcg gagtacgcga   240
acgcactgga gangggcctt cnggacccag tgctctacnt ggcgnanaag ttnncacngn   300
gtngcccttg cngcctgtnn nancngnacc anntgncggg acnntacanc tcggccacgc   360
tatgggtggc gttctgnttc tggctccttn tccaaggtgc tggtnctcnn anggnggccn   420
cgntctaant gnggtnnctt tgcnntgntt gntnccaccg gagccngtnn ngagcttcnt   480
tcngnggtgc tntntggtnt nggncg                                       506

<210> SEQ ID NO 7
<211> LENGTH: 450
<212> TYPE: DNA
<213> ORGANISM: Homo sapiens
<220> FEATURE:
<221> NAME/KEY: misc_feature
<223> OTHER INFORMATION: Incyte ID No: SBQA04510D1
<220> FEATURE:
<221> NAME/KEY: unsure
<222> LOCATION: 140, 165, 203, 237, 269, 289, 307, 338, 344, 347, 354,
              390, 430, 445
<223> OTHER INFORMATION: a, t, c, g, or other

<400> SEQUENCE: 7
gtcgactcta gaggatcccc ctgaacgaga ccattgacta caacgagcag ttcacctggc    60
gtctgaaaga gaattacgcc gcggagtacg cgaacgcact ggagaagggg ctgccggacc   120
cagtgctcta cctggcggan aagttcacac cgagtagccc ttgcngcctg taccaccagt   180
accacctggc gggacactac gcntcggcca cgctatgggt ggcgttctgc ttctggntcc   240
tctccaacgt gctgctctcc acgccggcnc cgctctacgg aggcctggna ctgctgacca   300 ccggagncctt cgcgctcttc ggggtcttcg ccttggcntc catntcnagc gtgncgctct   360
gccagatacg cctaggctcc tccgcgtcan caatcagtaa cggaacggct tctgggtcaa   420
gctggcaaan ggcgtcctgt gcctnttcct                                    450

<210> SEQ ID NO 8
<211> LENGTH: 250
<212> TYPE: DNA
<213> ORGANISM: Rattus norvegicus
<220> FEATURE:
<221> NAME/KEY: misc_feature
<223> OTHER INFORMATION: Incyte ID No: 259169_Rn.1

<400> SEQUENCE: 8
ggcgcctgaa tgaagactac accaaggagt atgttcaggc tctggagaag ggactgccgg    60
acccagtgct atacctggca gagaagttca caccgaacag tccttgcgga ttgtaccacc   120
aatatcacta tgccggtcac tatgccgggg caacgctatg ggtggcgttc tgcttctgga   180
```

-continued

```
tcatcgccaa tgcgctgctc tctatgcccg ctccgctcta tggaggtcta gctctgctca    240
tcacgggtgc                                                            250

<210> SEQ ID NO 9
<211> LENGTH: 1594
<212> TYPE: DNA
<213> ORGANISM: Mus musculus
<220> FEATURE:
<221> NAME/KEY: misc_feature
<223> OTHER INFORMATION: Incyte ID No: 110769_Mm.1

<400> SEQUENCE: 9
aggaacactg cgtgaagtcg cagggccagg aaagagtttc gggagatcac gcctctgcgc     60
ttcttaggag agccgcaggg ctcggacttt ttatcactca tcccagctcg ctgcctgcga    120
acagttctcg aacttcttgc aggatgactg cgtgggacgg ggtgctaccc ttttacccc    180 agcccaggca tgccgccagc ttcagcgtac cgctgctcat tgttatcctg gtgttcttgt    240
ctttggctgc tagcttcctg ttcatcttgc ctggaatccg tgggcactcg cgctggttct    300
ggttggtgag agtccttctt agcctgttca taggtgccga aattgtggct gtgcacttca    360
gtggagactg gttcgtgggg agagtgtgga ccaacacatc ctacaaagcc ttcagtccat    420
cccgtgttca agtccatgtc ggtctgcacg tggggctggc gggcgttaac attacactcc    480
gaggaacacc gaggcagcag ctgaacgaga ccattgacta caatgagcgt ttcacttggc    540
gtctgaacga agactacacc aaggagtatg tccatgcctt ggagaaggga ctgccggacc    600
cagtgctata cctggcagag aagttcacac cgagcagtcc ttgcgggctg taccaccaat    660
atcacctggc cggtcactat gccgcagcaa cactgtgggt ggcattctgc ttctggatca    720
tcgccaatgc gctgctctcc atgcccgccc cactctacgg aggcctggct tgctcacca    780 ccggtgcctt cacgctcttc ggtgtcttcg ccttcgcctc gatttccagc gtgccgctct    840
gccacttccg cctgggctcc gccgtcctca cgccttacta cggcgcctcc ttttggctca    900
cgctggccac cggcatcctg agcctcctcc tcggaggggc ggtggtgatt ctccactata    960
ctcggcccag cgcccttcgc tcctttctgg atctaagtgt caaagactgt agcaaccagg   1020
ctaaaggaaa ctcacctctc accctcaaca acccgcaaca cgaacagttg aagagtccag   1080
acttaaatat taccactctc ctgtgaaaat aactgactcc ggatttctac ccctctttgg   1140
gaccccatag acctgaagac tgtgttaaga gcgcgtgcca ggagcatagc ttagtctgga   1200
gaactgcttg tccctgcggg acgacaaggg ggcaccccat gtgcctttgc tctagagaat   1260
ggatttctca ggagaactgt aaataaactt ttttgtttct ttttttttct tcaaaattcc   1320
catgcccatc aatttccttg gcttctcttg gccatttgga gctacaacct tgagaaactc   1380
ctctaggcta gtaagagcct agtactgtat gtacattcag gtgctgagaa gcctgagaaa   1440
cacagtaggg ctctggggga ggtgcgccct ctagtgagat ctgagaggaa ctggcaggca   1500
tctcctccaa cgggtggtgg gttacgttct acccaaatct ctactagcca cactgaatgt   1560
attggggaag attaggattt tggcgttcat tcgc                               1594
```